United States Patent [19]

Kurahashi et al.

[11] Patent Number: 5,062,883
[45] Date of Patent: Nov. 5, 1991

[54] SPIRO-BENZYL-3-SUBSTITUTED PYRIDINES

[75] Inventors: Yoshio Kurahashi; Toshio Goto; Kunihiro Isono, all of Tokyo; Yoshinori Kitagawa, Tochigi; Tetsuji Izumi; Toshihito Kondo, both of Tokyo; Takayo Sato, Gunma, all of Japan

[73] Assignee: Nihon Tokushu Noyaku Seizo K.K., Tokyo, Japan

[21] Appl. No.: 518,640

[22] Filed: May 3, 1990

Related U.S. Application Data

[60] Division of Ser. No. 334,650, Apr. 6, 1989, Pat. No. 5,000,778, which is a continuation-in-part of Ser. No. 268,913, Nov. 8, 1988, Pat. No. 4,940,483.

[30] Foreign Application Priority Data

Nov. 10, 1987 [JP] Japan .................. 62-282211
May 30, 1988 [JP] Japan .................. 63-130168

[51] Int. Cl.$^5$ .................. C07D 405/06; C07D 409/06; A01N 43/40
[52] U.S. Cl. .................. 71/94; 514/336; 546/268; 546/283; 546/284
[58] Field of Search .................. 546/283, 268, 284; 514/336; 71/94

[56] References Cited

FOREIGN PATENT DOCUMENTS 0810675 4/1969 Canada .................. 71/94
1136104 12/1968 United Kingdom .................. 71/94

OTHER PUBLICATIONS

Chemical Abstracts, vol. 111(25) Abst. No. 232,780-t Dec. 18, 1989.
J. Med. Chem. vol. 12, p. 51, (1969).
Heterocycles, vol. 22, No. 5, 1984.
J. Chem. Soc. Perkin Trans. I 1984.
Bull. Soc. Chim. Belg. vol. 89 No. 1/1980.

*Primary Examiner*—Alan L. Rotman
*Attorney, Agent, or Firm*—Sprung Horn Kramer & Woods

[57] ABSTRACT

Fungicidal and herbicidal novel 3-substituted pyridines of the formula

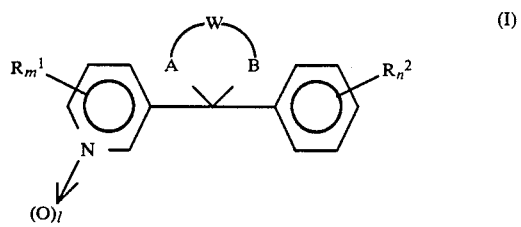

wherein
A represents oxygen or sulfur,
B represents oxygen, sulfur or sulfinyl,
$R^1$ represents hydrogen, halogen, alkyl or haloalkyl,
$R^2$ represents hydrogen, halogen, alkyl, phenyl, haloalkyl or phenoxy,
l is 0 or 1,
m is an integer from 1 to 4,
n is an integer from 1 to 5, and
W represents

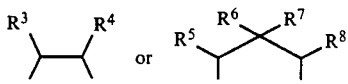

in which
$R^3$ and $R^4$ each represent hydrogen, hydroxyalkyl, alkoxyalkyl, alkyl, benzyloxyalkyl, haloalkyl or carboxyalkyl, or
$R^3$ and $R^4$ form a hydrocarbon ring having 3 to 12 carbon atoms in total together with the carbon atoms to which they are bonded, and
$R^5$, $R^6$, $R^7$ and $R^8$ each represent hydrogen, alkyl or hydroxyalkyl, provided that none of $R^1$, $R^2$, $R^3$, and $R^4$ represents a hydrogen atom when A and B each represents oxygen l is 0 and W represents

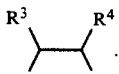

6 Claims, No Drawings

SPIRO-BENZYL-3-SUBSTITUTED PYRIDINES

This is a division of application Ser. No. 334,650, filed Apr. 6, 1989, now allowed, which is a continuation-in-part of application Ser. No. 268,913, filed Nov. 8, 1988, now U.S. Pat. No. 4,940,483.

The present invention relates to novel 3-substituted pyridines, to several processes for their preparation, and to their use as agricultural and horticultural fungicides and herbicides.

It has already been disclosed that 2-phenyl-2-(pyridin-4-yl)-1,3-dioxolane was a reaction intermediate (see Heterocycles, 22, 1137 (1984)), 2-phenyl-2-(pyridin-4-yl)-1,3-dithiolane and 2-phenyl-2-(pyridin-4-yl)-1,3-dithiane were reaction intermediates [see J. Chem. Soc. Perkin Trans., I, 1223 (1984)] and 2-phenyl-2-(pyridin-3-yl)-1,3-dioxolane was a reaction intermediate [see Bull. Soc. Chim. Belg., 89, 67 (1980)].

There have been found novel 3-substituted pyridines of the formula (I)

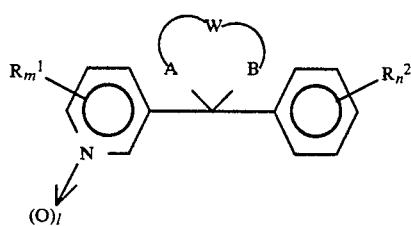

wherein
A represents oxygen or sulfur,
B represents oxygen, sulfur or sulfinyl,
$R^1$ represents hydrogen, halogen, alkyl or haloalkyl,
$R^2$ represents hydrogen, halogen, alkyl, phenyl, haloalkyl or phenoxy,
l is 0 or 1,
m is an integer from 1 to 4,
n is an integer from 1 to 5, and
W represents

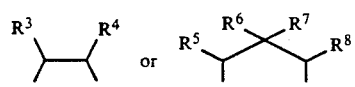

in which
$R^3$ and $R^4$ each represents hydrogen, hydroxyalkyl, alkoxyalkyl, alkyl, benzyloxyalkyl, haloalkyl or carboxyalkyl, or
$R^3$ and $R^4$ form a hydrocarbon ring having 3 to 12 carbon atoms in total together with the carbon atoms to which they are bonded, and
$R^5$, $R^6$, $R^7$ and $R^8$ each represents hydrogen, alkyl or hydroxyalkyl, provided that none of $R^1$, $R^2$, $R^3$ and
$R^4$ represents a hydrogen atom when A and B both represent an oxygen atom, l is 0 and W represents

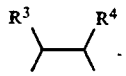

3-Substituted pyridines of the formula (I) are obtained when a) in the case where l is 0 and B represents oxygen or sulfur:
a compound of the formula (II):

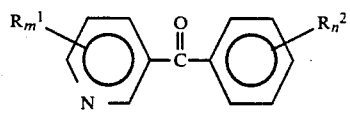

wherein $R^1$, $R^2$, m and n are as defined above, is reacted with a compound of the formula (III):

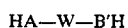

HA—W—B'H (III)

wherein
A and W are as defined above, and
B' represents oxygen or sulfur,
in the presence of an inert solvent, and in the presence of an acid catalyst, or b) in the case where l is 1, and A and B each represents oxygen:
a compound of the formula (Ib)

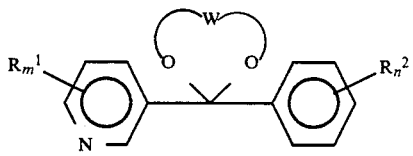

wherein $R^1$, $R^2$, m, n and W are as defined above, is reacted with an oxidizing agent, in the presence of an inert solvent, or c) in the case where B represents a sulfinyl group and l is 0:
a compound of the formula (Ic)

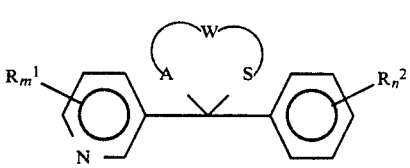

wherein $R^1$, $R^2$, m, n, A and W are as defined above,
is reacted with an oxidizing agent, in the presence of an inert solvent.

The novel 3-substituted pyridines exhibit powerful fungicidal and herbicidal properties.

Surprizingly, the 3-substituted pyridines according to the invention exhibit a substantially greater fungicidal and herbicidal action than those known from the prior art, for instance, abovementioned Bull. Soc. Chim. Belg., 89, 67 (1980), J. Chem. Soc. Perkin Trans. I 1223 (1984) and Heterocycles 22 1137 (1984).

Among the 3-substituted pyridines according to the invention of the formula (I), preferred compounds are those wherein A and B each represents oxygen or sulfur, $R^1$ represents hydrogen or chlorine, $R^2$ represents hydrogen, chlorine, bromine, fluorine, alkyl having 1 to 4 carbon atoms, or phenyl, m and n are each 1 or 2, and W represents

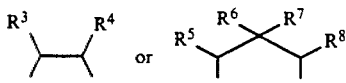

in which
- R³ and R⁴ each represents hydrogen, alkyl having 1 to 6 carbon atoms, hydroxyalkyl having 1 to 3 carbon atoms, alkoxyalkyl having 2 to 4 carbon atoms in total, or haloalkyl having 1 to 4 carbon atoms, or
- R³ and R⁴ form a hydrocarbon ring having 6 to 12 carbon atoms in total together with the carbon atoms to which they are bonded, and
- R⁵, R⁶, R⁷ and R⁸ each represents hydrogen, alkyl having 1 to 4 carbon atoms or hydroxyalkyl having 1 to 4 carbon atoms, provided that none of R¹, R², R³ and R⁴ represents hydrogen when A and B each represents oxygen and, l is 0

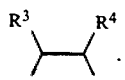

Very particularly preferred 3-substituted pyridines of the formula (I) are those wherein A and B each represents oxygen or sulfur,
R¹ represents hydrogen, or chlorine,
R² represents hydrogen, chlorine, bromine, fluorine or methyl, or phenyl
n and m are each 1 or 2, and W represents

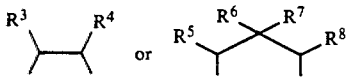

in which
- R³ and R⁴ each represents hydrogen, alkyl having 1 to 4 carbon atoms, methoxymethyl or chloromethyl, or
- R³ and R⁴ form a cyclohexane ring together with the carbon atoms to which they are bonded, and
- R⁵, R⁶, R⁷ and R⁸ each represents hydrogen or alkyl having 1 to 3 carbon atoms, provided that none of R¹, R², R³ and R⁴ represents a hydrogen atom when A and B each represent oxygen, l is 0 and W represents

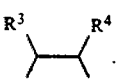

Specifically, the following compounds may be mentioned:
2-phenyl-2-(pyridin-3-yl)-1,3-dithiolane,
4-methyl-2-phenyl-2-(pyridin-3-yl)-1,3-dithiolane.
2-(2,4-dichlorophenyl)-5,5-diethyl-2-(3-pyridyl)-1,3-dioxane,
2-(4-chlorophenyl)-5,5-dimethyl-2-(3-pyridyl)-1,3-dioxane,
2-(biphenyl-4-yl)-5,5-diethyl-2-(3-pyridyl)-1,3-dioxane and
2-(2,4-dichlorophenyl)-5-ethyl-5-propyl-2-(3-pyridyl)-1,3-dioxane.

When in the process a), for example, 3-benzoylpyridine and 1,2-propanediol are used as starting materials, the course of the reaction can be represented by the following equation:

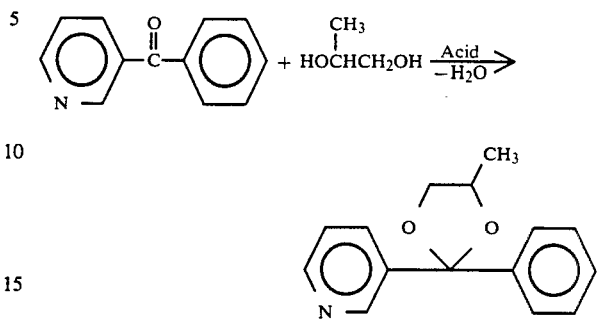

When in the process b), for example, 4-tert.-butyl-2-phenyl-2-(pyridin-3-yl)-1,3-dioxolane and m-chloroperbenzoic acid are used as starting materials, the course of the reaction can be represented by the following equation:

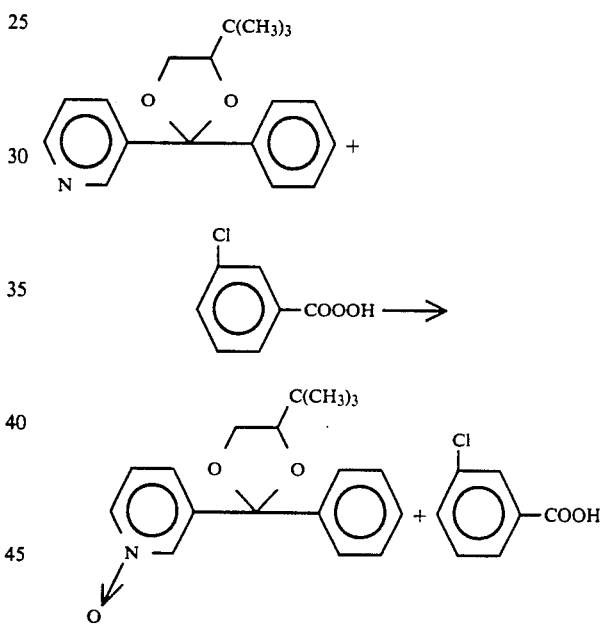

When in the process c, for example, 2-phenyl-2-(pyridin-3-yl)-1,3-dithiane and m-chloroperbenzoic acid are used as starting materials, the course of the reaction can be represented by the following equation:

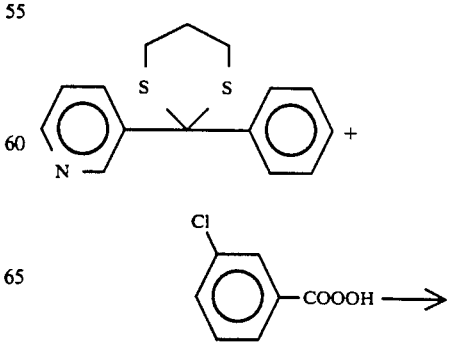

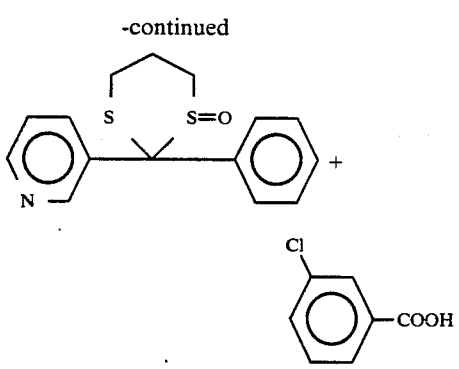

In the process a), the starting compounds of the formulae (II) and (III) mean compounds based on the above definition of $R^1$, $R^2$, m, n, A, B' and W, preferably compounds based on the above preferred definitions.

The compounds of the formulae (II) and (III) are known. 3-Benzoylpyridine can be cited as an example of the formula (II).

1,2-Ethane dithiol and 1,2-propane dithiol can be cited as examples of the formula (III).

In the processes b) and c), the starting compounds of the formulae (Ib) and (Ic) mean compounds based on the above definition of $R^1$, $R^2$, m, n, A and W, preferably compounds based on the above preferred definitions.

The compounds of the formula (Ib) and (Ic) can be prepared according to the above-mentioned process a). 4-tert.-butyl-2-(4-chlorophenyl)-2-(pyridin-3-yl)-1,3-dioxolane can be cited as an example of the formula (Ib) and 2-phenyl-2-(pyridin-3-yl)-1,3-dithiolane and 4-methyl-2-phenyl-2-(pyridin-3-yl)-1,3-dithiolane can be cited as examples of the formula (Ic).

In the processes b) and c), hydrogen peroxide and m-chloroperbenzoic acid can be cited as examples of an oxidizing agent.

In carrying out process a), it is possible to use any inert organic solvents as the suitable diluents. Examples of the diluents are aliphatic, cycloaliphatic and aromatic hydrocarbons which may be chlorinated hexane, cyclohexane, petroleum ether, ligroin, benzene, toluene, xylene, methylene chloride, chloroform, carbon tetrachloride, ethylene chloride, chlorobenzene, and the like; ethers such as diethyl ether, methyl ethyl ether, di-isopropyl ether, dibutyl ether, propylene oxide, dioxane, tetrahydrofuran, and the like; ketones such as acetone, methyl ethyl ketone, methyliso-propyl ketone, methyliso-butyl ketone, and the like; nitriles such as acetonitrile, propionitrile and acrylonitrile; alcohols such as iso-propanol; esters such as, for example, ethyl acetate, amyl acetate, and the like; acid amides such as dimethyl formamide and dimethyl acetoamide; and sulfones and sulfoxides such as dimethyl sulfoxide, sulfolane, and the like.

The process a) may be carried out in the presence of acid catalysts and as such catalyst may be mentioned, for example, sulfuric acid, hydrochloric acid, acid ion exchanging resin, methane sulfonic acid, ammonium chloride, para-toluene sulfonic acid, trifluoroboron-ether complex, aluminum chloride, zinc chloride and paratoluene sulfonic acid pyridinium salt.

In the process a), the reaction temperature can be varied within a substantially wide range. For instance, the reaction may be effected at a temperature between about $-10°$ C. and about 200° C., preferably at a temperature of from about 50° C. to about 150° C. It is preferred to carry out the reaction under normal pressure, although the use of a higher or lower pressure is also allowable.

In carrying out the reaction of the process a), use is made, for example, of the compounds of the formula (III) in the mol amount from 1 to 10 times and an acid catalyst in the amount of from 0.1 to 3 times, respectively, the mol amount of the above-mentioned compounds of the formula (II) in the presence of an inert solvent such as, for example, toluene, to obtain the desired compound.

In carrying out the reaction of the above-mentioned processes b) and c), use is made, as oxidizing agent, of organic peroxides such as meta-chloroperbenzoic acid and hydrogen peroxide.

In carrying out the above-mentioned processes b) and c) with the use of organic peroxide as oxidizing agent, use may be made, as proper diluents, of any kind of inert organic solvents.

When the oxidizing agent is organic peroxide, examples of the diluents are aliphatic, cycloaliphatic and aromatic hydrocarbons which may be chlorinated such as hexane, cyclohexane, petroleum ether, ligroin, benzene, toluene, xylene, methylene chloride, chloroform, carbon tetrachloride, ethylene chloride, chlorobenzene, and the like; alcohols such as methanol, ethanol, iso-propanol, butanol and ethylene glycol; esters such as, for example, ethyl acetate, amyl acetate and the like; and acid amides such as dimethylformamide and dimethylacetamide.

In carrying out the above-mentioned processes b) and c) with the use of hydrogen peroxide as oxidizing agent, the diluents to be used therein may be, for example, water that may be basic, neutral or acid, alcohols such as, for example, methanol, ethanol, iso-propanol, butanol and ethylene glycol; and carboxylic acids such as, for example, acetic acid.

In each of the processes b) and c), the reaction temperature can be varied within a substantially wide range. When use is made, as oxidizing agent, of organic peroxide, the reaction, in general, may be effected at a temperature between about $-10°$ C. and about 50° C., preferably at a temperature of from about 0° C. to about 30° C.

Further, when use is made, as oxidizing agent, of hydrogen peroxide, the reaction, in general, may be effected at a temperature between about $-10°$ C. and about 100° C., preferably at a temperature of from about 0° C. to about 30° C. It is preferred to carry out the reaction under normal pressure, although the use of a higher or lower pressure is also allowable.

In carrying out the reaction of the process b), use is made, for example, of meta-chloroperbenzoic acid in the mol amount from 1 to 2 times the mol amount of the above-mentioned compounds of the formula (Ib) in the presence of an inert solvent such as, for example, methylene chloride to obtain the desired compound.

In carrying out the reaction of the above-mentioned process c), use is made of meta-chloroperbenzoic acid in the mol amount of from 1 to 1.2 times the mol amount of the above-mentioned compounds of the formula (Ic) in the presence of inert organic solvents such as methylene chloride to obtain the desired compound.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonoadaceae, Rhizobiaceae, Enterobacteriaceae, Corynebacteriaceae and Streptomycetaceae.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

Some causative organisms of fungal and bacterial diseases included under the abovementioned main headings, are mentioned below as non-limiting examples:

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as for example, *Phytophthora infestans;*

Pseudoperonospora species, such as, for example, *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (Conidial form: Drechslera, Synonym: Helminthosporium);

Cochliobolus species, such as, for example, *Cochliobolus sativus* (Conidial form: Drechslera, Synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can also be used as weedkillers, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents, diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds, as fungicides, according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporising, injecting, forming a slurry, brushing on, dusting, scatterting, dry dressing, moist dressing, wet dressing, slurry dressing or encrusting.

In the treatment of parts of plants, the active compound concentrations, as fungicides in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed.

The active compounds, as herbicides according to the invention, as such or in the form of their formulations, can also be used, for combating weeds, as mixtures with known herbicides, finished formulations or tank mixes being possible.

The active compounds, as herbicides according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.1 and 10 kg of active compound per hectare of soil surface, preferably between 0.5 and 5 kg per ha.

The preparation and use of the active compounds according to the invention can be seen from the following examples.

PREPARATION EXAMPLES

Example 1:

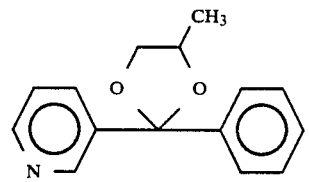 (Compound No. 6)

1.83 g of 3-benzoylpyridine, 1.44 g of 1,2-propanediol and 2.43 g of p-toluenesulfonic acid monohydrate were dissolved in a mixture of 15 ml of toluene and 15 ml of n-butanol and the resulting mixture was heated under reflux while removing the water thus formed therefrom. After the completion of the reaction, the solvents were distilled off in vacuo. The residue was dissolved in dichloromethane, washed with an aqueous solution of sodium hydroxide and then with water and then dried over anhydrous sodium sulfate. After filtering off the sodium sulfate, the solvent was distilled off in vacuo to thereby give 4-methyl-2-phenyl-2-(pyridin-3-yl)-1,3-dioxolane, m.p.: 40°-44° C.

Example 2:

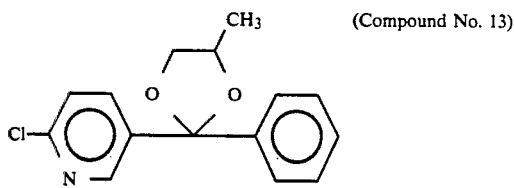
(Compound No. 13)

To 25 ml of a solution of 1.5 g of 3-benzoyl-6-chloropyridine and 3.2 g of 1,2-propanediol in toluene, 1.2 g of boron trifluoride etherate was added. The resulting mixture was heated under reflux for six hours while removing the water thus formed therefrom. Then the reaction mixture was cooled, poured into an aqueous solution of sodium hydroxide and extracted with ether. The organic phase was washed with water and dried over anhydrous sodium sulfate. After filtering off the sodium sulfate and distilling off the solvent in vacuo, 2-(6-chloropyridin-3-yl)-4-methyl-2-phenyl-1,3-dioxolane was obtained, m.p.: 44°–51° C.

Example 3:

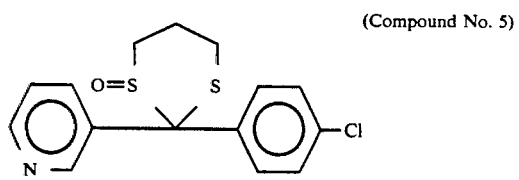
(Compound No. 5)

To 10 ml of a solution of 1.1 g of 2-(4-chlorophenyl)-2-(pyridin-3-yl)-1,3-dithiane in methylene chloride, 1.3 g of m-chloroperbenzoic acid was added under ice-cooling. The resulting mixture was stirred under ice-cooling for 30 minutes and then at room temperature for one hour followed by heating under reflux. After the completion of the reaction, the crystals thus precipitated were filtered off to thereby give 2-(4-chlorophenyl)-2-(pyridin-3-yl)-1,3-dithiane-1-oxide, $n_D^{20}$: 1.3305.

Example 4:

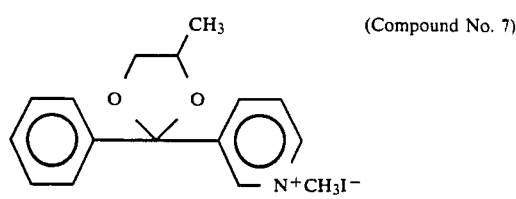
(Compound No. 7)

2.4 g of 4-methyl-2-phenyl-2-(pyridin-3-yl)-1,3-dioxolane was dissolved in a small amount of ethanol and 1.7 g of methyl iodide was added thereto. The resulting mixture was stirred at room temperature for four hours. After distilling off the solvent, the crystals thus obtained were washed with dry ethanol to thereby give 4-methyl-2-phenyl-2-(pyridin-3-yl)-1,3-dioxolane methiodide, m.p.: 125°–132° C.

Example 5:

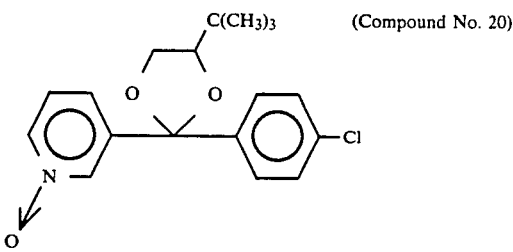
(Compound No. 20)

To 10 ml of a solution of 0.63 g of 4-tert-butyl-2-(4-chlorophenyl)-2-(pyridin-3-yl)-1,3-dioxolane in methylene chloride, 0.22 g of m-chloroperbenzoic acid was added and the resulting mixture was stirred at room temperature. After the completion of the reaction, the reaction mixture was poured into an aqueous solution of sodium hydroxide and extracted with methylene chloride. The organic phase was washed with water and dried over anhydrous sodium sulfate. After filtering off the sodium sulfate and distilling off the solvent in vacuo, 4-tert-butyl-2-(4-chlorophenyl)-2-(pyridine N-oxide-3-yl)-1,3-dioxolane was obtained.

Table 1 shows the compounds of the present invention which may be obtained by the same methods as the above examples.

TABLE 1

| Comp. No. | $R_m^1$ (ring) | $R_n^2$ (ring) | A | B | W | Physical Properties |
|---|---|---|---|---|---|---|
| 1 | pyridine | phenyl | S | S | —CH$_2$CH$_2$— | mp. 60–61 |

TABLE 1-continued
| | | | | | | |
|---|---|---|---|---|---|---|
| 2 | 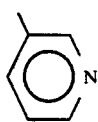 | 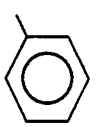 | S | S | $-CH_2CH(CH_3)-$ | $n_D^{20}$ 1.6439 |
| 3 | 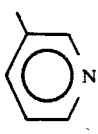 | 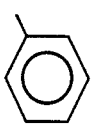 | S | S | $-CH_2CH_2CH_2-$ | mp. 96–98 |
| 4 | 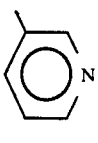 | 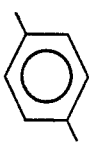 | S | S | $-CH_2CH_2CH_2-$ | $n_D^{20}$ 1.5820 |
| 5 | 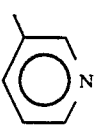 | 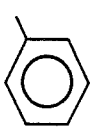 | S | $-S(=O)-$ | $-CH_2CH_2CH_2-$ | |
| 6 | 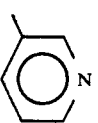 | 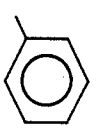 | O | O | $-CH_2CH(CH_3)-$ | mp. 40–44 |
| 7 | 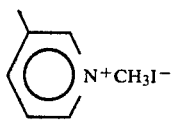 | 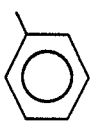 | O | O | $-CH_2CH(CH_3)-$ | mp. 125–132 |
| 8 | 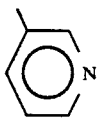 | 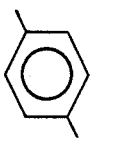 | O | O | $-CH_2CH(CH_3)-$ | $n_D^{20}$ 1.5600 |
| 9 | 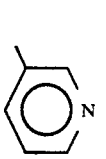 | 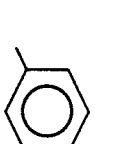 | O | O | $-CH_2CH(CH_3)-$ | $n_D^{20}$ 1.5675 |
| 10 | 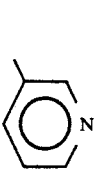 | 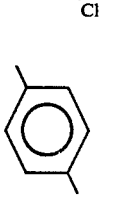 | O | O | $-CH_2CH(CH_3)-$ | $n_D^{20}$ 1.5812 |
| 11 | 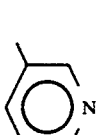 | 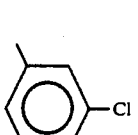 | O | O | $-CH_2CH(CH_3)-$ | $n_D^{20}$ 1.5680 |

TABLE 1-continued

| | | | | | | |
|---|---|---|---|---|---|---|
| 12 |  | 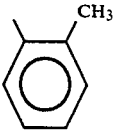 CH₃ | O | O | $-CH_2\underset{\underset{CH_3}{\mid}}{CH}-$ | $n_D^{20}$ 1.5646 |
| 13 |  | 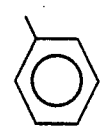 | O | O | $-CH_2\underset{\underset{CH_3}{\mid}}{CH}-$ | mp. 44–51 |
| 14 | 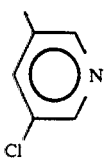 | 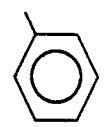 | O | O | $-CH_2\underset{\underset{CH_3}{\mid}}{CH}-$ | $n_D^{20}$ 1.5730 |
| 15 | 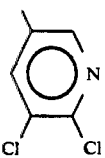 | 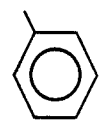 | O | O | $-CH_2\underset{\underset{CH_3}{\mid}}{CH}-$ | $n_D^{20}$ 1.5718 |
| 16 | 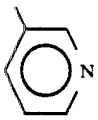 |  | O | O | $-CH_2\underset{\underset{CH_2CH_3}{\mid}}{CH}-$ | $n_D^{20}$ 1.5485 |
| 17 | 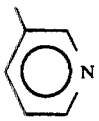 |  | O | O | $-CH_2\underset{\underset{CH_2CH_2CH_3}{\mid}}{CH}-$ | $n_D^{20}$ 1.5290 |
| 18 | 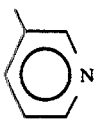 | 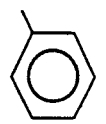 | O | O | $-CH_2\underset{\underset{CH_2CH_2CH_2CH_3}{\mid}}{CH}-$ | $n_D^{20}$ 1.5305 |
| 19 | 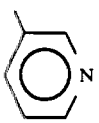 |  | O | O | $-CH_2\underset{\underset{C(CH_3)_3}{\mid}}{CH}-$ | mp. 42–47 |
| 20 | 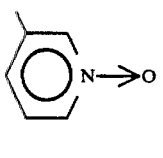 | 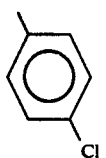 | O | O | $-CH_2\underset{\underset{C(CH_3)_3}{\mid}}{CH}-$ | $n_D^{20}$ 1.545 Oily |
| 21 | 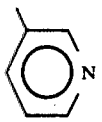 |  | O | O | $-CH_2\underset{\underset{CH_2(CH_2)_4CH_3}{\mid}}{CH}-$ | $n_D^{20}$ 1.5188 |

TABLE 1-continued
| 22 | 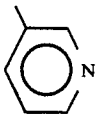 | 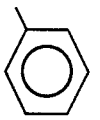 | O | O | −CH₂CH−\|CH₂Cl | $n_D^{20}$ 1.5705 |
|---|---|---|---|---|---|---|
| 23 | 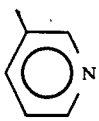 |  | O | O | −CH₂CH−\|CH₂Cl | Oily |
| 24 | 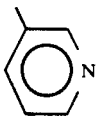 | 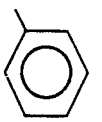 | O | O | −CH₂CH−\|CH₂OH | $n_D^{20}$ 1.5757 |
| 25 | 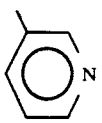 |  | O | O | −CH₂CH−\|CH₂OH | $n_D^{20}$ 1.5931 |
| 26 | 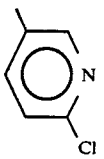 | 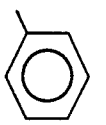 | O | O | −CH₂CH−\|CH₂OH | $n_D^{20}$ 1.5820 |
| 27 | 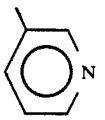 | 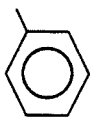 | O | O | −CH₂CH−\|CH₂OCH₃ | $n_D^{20}$ 1.5550 |
| 28 | 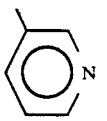 | 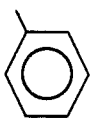 | O | O | −CH₂CH−\|CH₂OCH₂−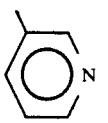 | $n_D^{20}$ 1.5784 |
| 29 | 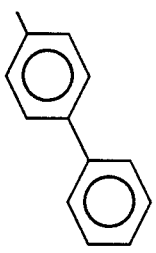 | 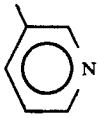 | S | $-\overset{O}{\underset{\|}{S}}-$ | −CH₂CH−\|CH₃ | |
| 30 |  | 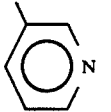 | O | O | −CH₂CH−\|CH(OH)CH₃ | $n_D^{20}$ 1.5578 |
| 31 | 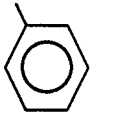 | | O | O | −CH−CH−\|  \|\nCH₃ CH₃ | mp. 108−115 |

TABLE 1-continued

| | | | | | |
|---|---|---|---|---|---|
| 32 | 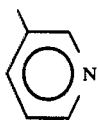 | O | O | 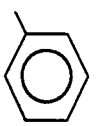 | mp. 111-119 |
| 33 | 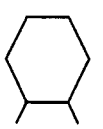 | O | O | 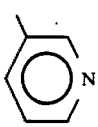 | $n_D^{50}$ 1.525–1.530 |
| 34 | 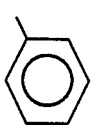 | O | O | —CH$_2$CH$_2$CH$_2$— | mp. 73-81 |
| 35 | 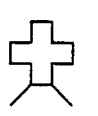 | O | O | $\begin{array}{c}\text{CH}_3\\|\\-\text{CH}_2\text{CH}_2\text{CH}-\end{array}$ | mp. 67-73 |
| 36 | 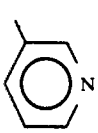 | O | O | $\begin{array}{c}\text{H}_3\text{C}\quad\text{CH}_3\\-\text{CH}_2-\text{C}-\text{CH}_2-\end{array}$ | mp. 88-92 |
| 37 | 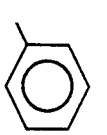 | O | O | $\begin{array}{c}\text{H}_3\text{C}\quad\text{CH}_2\text{CH}_2\text{CH}_3\\-\text{CH}_2-\text{C}-\text{CH}_2-\end{array}$ | $n_D^{50}$ 1.5350 |
| 38 | 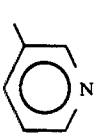 | O | O | $\begin{array}{c}\text{CH}_3\quad\text{CH}_3\\|\qquad|\\-\text{CH}-\text{CH}_2-\text{CH}-\end{array}$ | mp. 102-104 |
| 39 | 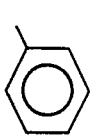 | O | O | $\begin{array}{c}\text{H}_3\text{CH}_2\text{C}\quad\text{CH}_2\text{CH}_3\\-\text{CH}_2-\text{CH}-\text{CH}-\end{array}$ | $n_D^{20}$ 1.5403 |
| 40 |  | O | O | $\begin{array}{c}\text{HOH}_2\text{C}\quad\text{CH}_2\text{OH}\\-\text{CH}_2-\text{C}-\text{CH}_2-\end{array}$ | $n_D^{20}$ 1.5765 |
| 41 | 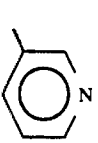 | O | O | $\begin{array}{c}\text{CH}_3\quad\text{CH}_3\\|\qquad|\\-\text{CH}-\text{CH}-\end{array}$ | $n_D^{20}$ 1.5563 |
| 42 | 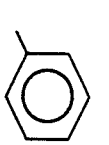 | O | O | $\begin{array}{c}\text{H}_3\text{C}-\text{H}_2\text{C}\quad\text{CH}_2-\text{CH}_3\\-\text{CH}_2-\text{C}-\text{CH}_2-\end{array}$ | $n_D^{20}$ 1.5340 |

TABLE 1-continued

| # | Ar1 | Ar2 | X | Y | R | notes |
|---|---|---|---|---|---|---|
| 43 | 3-methylpyridyl | 2,4-dichlorophenyl | S | S(=O) | -CH(CH3)-CH(CH3)- | |
| 44 | 3-methylpyridyl | 4-methylbiphenyl | S | S(=O) | -CH(CH3)-CH(CH3)- | |
| 45 | 3-methylpyridyl | 2-chlorophenyl | O | O | -CH2-CH(C(CH3)3)- | |
| 46 | 3-methylpyridyl | 2,3-dichlorophenyl | O | O | -CH2-CH(C(CH3)3)- | |
| 47 | 3-methylpyridyl | 2,4-dichlorophenyl | O | O | -CH2-CH(C(CH3)3)- | $n_D^{20}$ 1.5455 |
| 48 | 3-methylpyridyl | 3,4-dichlorophenyl | O | O | -CH2-CH(C(CH3)3)- | $n_D^{20}$ 1.5330 |
| 49 | 3-methylpyridyl | pentachlorophenyl | O | O | -CH2-CH(C(CH3)3)- | |
| 50 | 3-methylpyridyl | 4-fluorophenyl | O | O | -CH2-CH(C(CH3)3)- | |
| 51 | 3-methylpyridyl | 3-methylphenyl | O | O | -CH2-CH(C(CH3)3)- | |

TABLE 1-continued
| | | | | | | |
|---|---|---|---|---|---|---|
| 52 | 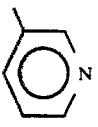 | 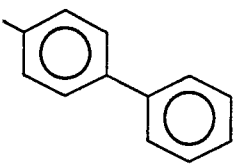 | O | O | −CH₂CH− with C(CH₃)₃ | mp. 87–100 |
| 53 | 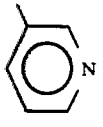 | 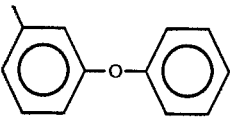 | O | O | −CH₂CH− with C(CH₃)₃ | $n_D^{20}$ 1.5592 |
| 54 | 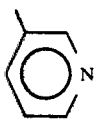 |  | S | −S(=O)− | −CH₂−CH₂−CH₂− | |
| 55 | 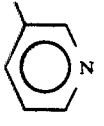 | 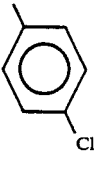 | O | O | −CH₂CH− with C(CH₃)₃ | $n_D^{20}$ 1.5750 |
| 56 | 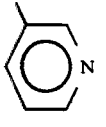 |  | O | O | −CH₂−C(CH₂CH₃)(CH₂CH₃)−CH₂− | $n_D^{20}$ 1.5519 |
| 57 | 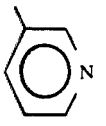 |  | S | S | −CH₂−CH₂− | $n_D^{20}$ 1.6545 |
| 58 | 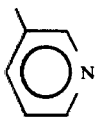 |  | S | S | −CH₂−CH(CH₃)− | $n_D^{22.5}$ 1.6394 |
| 59 | 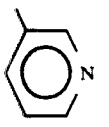 | 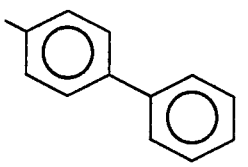 | S | S | −CH₂−CH(CH₃)− | $n_D^{20}$ 1.6752 |
| 60 | 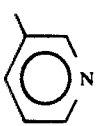 |  | S | S | −CH₂−CH(CH₃)− | $n_D^{20}$ 1.6286 |

TABLE 1-continued
| 61 | 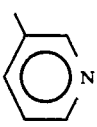 | 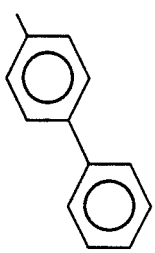 | S | $\overset{O}{\underset{\|}{-S-}}$ | —CH₂CH₂CH₂— | |
|---|---|---|---|---|---|---|
| 62 |  | 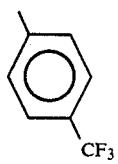 | S | S | —CH₂CH₂— | |
| 63 | 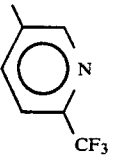 | 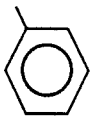 | S | S | —CH₂CH₂— | |
| 64 | 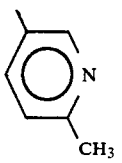 | 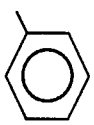 | S | S | —CH₂CH₂— | |
| 65 | 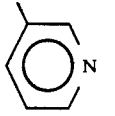 |  | S | $\overset{O}{\underset{\|}{-S-}}$ | —CH₂CH₂— | |
| 66 | 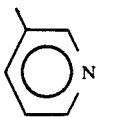 | 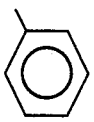 | S | $\overset{O}{\underset{\|}{-S-}}$ | $-CH_2\overset{CH_3}{\underset{\|}{CH}}-$ | |
| 67 | 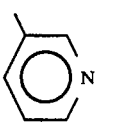 | 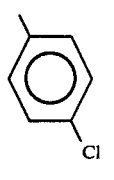 | S | $\overset{O}{\underset{\|}{-S-}}$ | —CH₂—CH₂—CH₂— | $n_D^{20}$ 1.3305 |
| 68 | 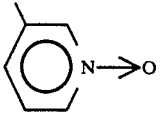 | 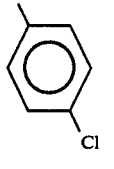 | O | O | $-CH_2\overset{CH_2Cl}{\underset{\|}{CH}}-$ | |
| 69 | 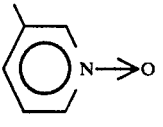 | 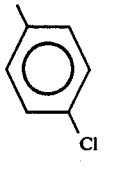 | O | O | $-CH_2\overset{CH_3}{\underset{\|}{CH}}-$ | |

TABLE 1-continued
| 70 | 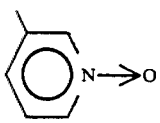 | 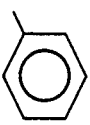 | O | O | —CH$_2$CH— with C(CH$_3$)$_3$ | |
| --- | --- | --- | --- | --- | --- | --- |
| 71 | 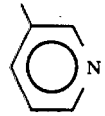 | 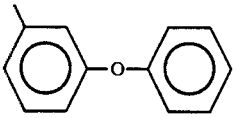 | S | S | —CH$_2$CH— with CH$_3$ | $n_D^{20}$ 1.5828 |
| 72 | 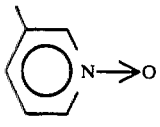 |  | O | O | —CH$_2$CH— with C(CH$_3$)$_3$ | oily |
| 73 | 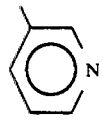 | 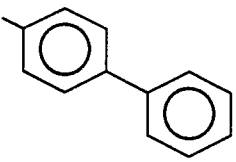 | O | O | 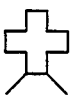 | mp. 81–90° C. |
| 74 | 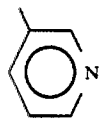 | 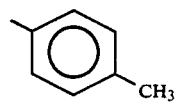 | O | O | —CH$_2$—C(CH$_2$CH$_3$)(CH$_2$CH$_3$)—CH$_2$— | $n_D^{20}$ 1.5470 |
| 75 | 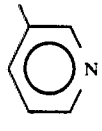 |  | O | O | —CH$_2$—C(CH$_2$CH$_3$)(CH$_2$CH$_3$)—CH$_2$— | $n_D^{20}$ 1.5720 |
| 76 | 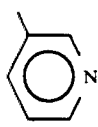 | 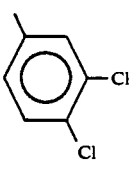 | O | O | —CH$_2$—C(CH$_2$CH$_3$)(CH$_2$CH$_3$)—CH$_2$— | $n_D^{20}$ 1.5548 |
| 77 | 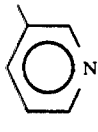 |  | O | O | —CH$_2$CH$_2$— | |
| 78 |  | 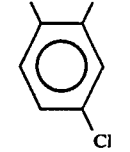 | O | O | —CH$_2$CH$_2$— | |

-continued
| | | | | |
|---|---|---|---|---|
| 79 | 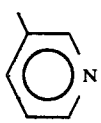 | 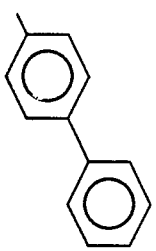 | O  O | —CH₂CH₂— |
| 80 | 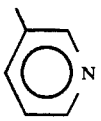 | 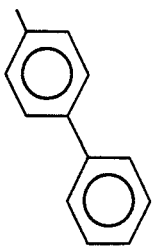 | O  O | $-CH_2\overset{CH_3}{\underset{\|}{CH}}-$ |
| 81 | 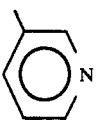 | 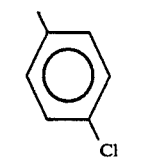 | O  O | $-CH_2\overset{CH_2CH_3}{\underset{\|}{CH}}-$ |
| 82 | 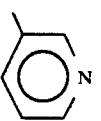 | 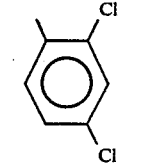 | O  O | $-CH_2\overset{CH_2CH_3}{\underset{\|}{CH}}-$ |
| 83 | 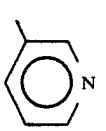 | 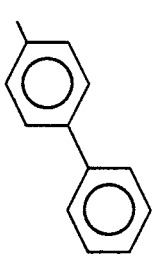 | O  O | $-CH_2\overset{CH_2CH_3}{\underset{\|}{CH}}-$ |
| 84 | 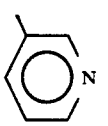 | 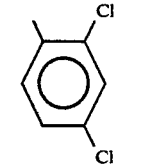 | O  O | $-CH_2\overset{CH_2CH_2CH_3}{\underset{\|}{CH}}-$ |
| 85 | 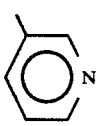 | 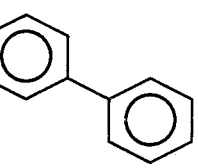 | O  O | $-CH_2\overset{CH_2CH_2CH_3}{\underset{\|}{CH}}-$ |
| 86 | 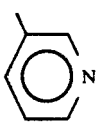 | 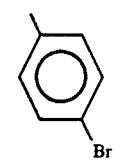 | O  O | $-CH_2\overset{CH(CH_3)_2}{\underset{\|}{CH}}-$ |

-continued
| | | | | | |
|---|---|---|---|---|---|
| 87 | 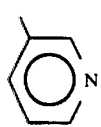 |  | O | O | 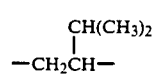 |
| 88 | 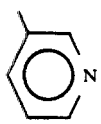 |  | O | O | 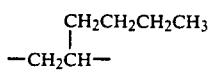 |
| 89 | 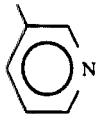 | 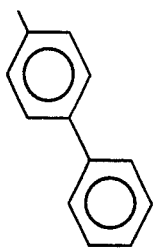 | O | O | 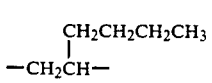 |
| 90 | 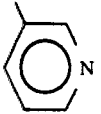 | 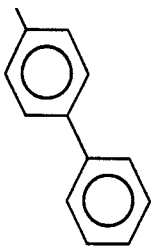 | O | O | 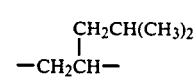 |
| 91 | 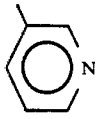 | 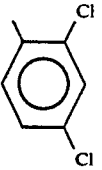 | O | O | 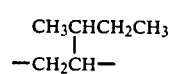 |
| 92 | 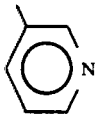 | 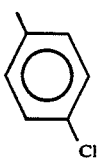 | O | O | 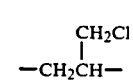 oily |
| 93 | 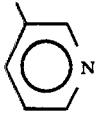 |  | O | O | 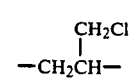 |
| 94 | 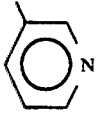 |  | O | O | 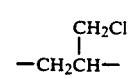 |

-continued
| | | | | | |
|---|---|---|---|---|---|
| 95 | 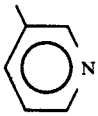 | 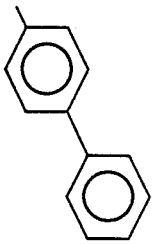 | O | O | 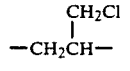 |
| 96 | 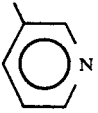 | 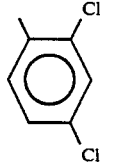 | O | O | —CH$_2$CH$_2$CH$_2$— |
| 97 | 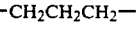 | 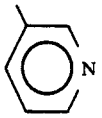 | O | O | —CH$_2$CH$_2$CH$_2$— mp. 143–144.5° C. |
| 98 | 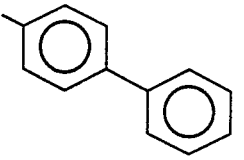 | 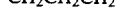 | O | O | 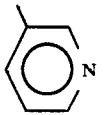 |
| 99 | 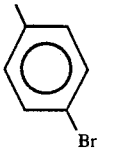 | 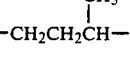 | O | O | 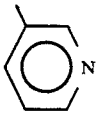 |
| 100 | 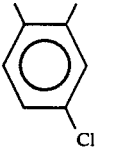 | 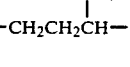 | O | O | 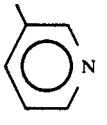 mp. 111–115° C. |
| 101 | 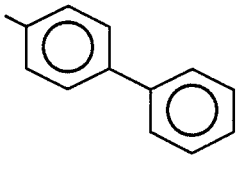 | 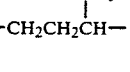 | O | O | 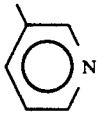 |
| 102 | 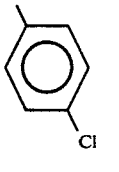 | 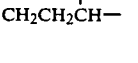 | O | O | 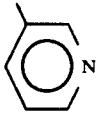 |

| | | | | |
|---|---|---|---|---|
| 103 | 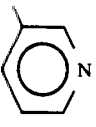 | 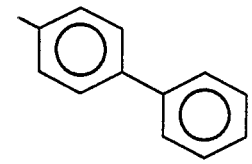 | O O | CH₂CH₃<br>\|<br>—CH₂CH₂CH— |
| 104 | 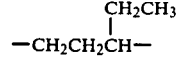 |  | O O | CH(CH₃)₂<br>\|<br>—CH₂CH₂CH— |
| 105 | 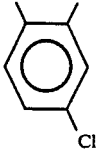 | 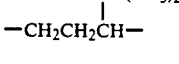 | O O | CH(CH₃)₂<br>\|<br>—CH₂CH₂CH— |
| 106 |  | 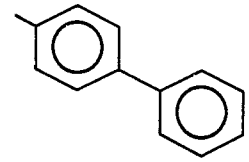 | O O | CH₂CH₂CH₃<br>\|<br>—CH₂CH₂CH— |
| 107 | 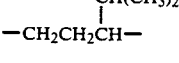 |  | O O | CH₂CH₂CH₃<br>\|<br>—CH₂CH₂CH— |
| 108 |  | 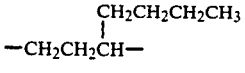 | O O | CH₂CH(CH₃)₂<br>\|<br>—CH₂CH₂CH— |
| 109 | 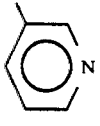 | 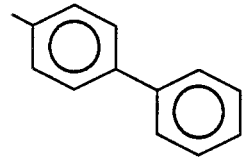 | O O | CH₃CHCH₂CH₃<br>\|<br>—CH₂CH₂CH— |
| 110 | 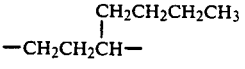 | 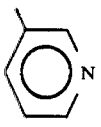 | O O | C(CH₃)₃<br>\|<br>—CH₂CH₂CH— |
| 111 |  | 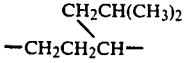 | O O | CH₃<br>\|<br>—CH₂CHCH₂— |

-continued
| | | | | | |
|---|---|---|---|---|---|
| 112 | 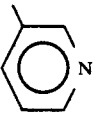 | 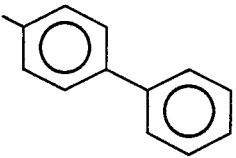 | O | O | −CH$_2$CH(CH$_3$)CH$_2$− |
| 113 | 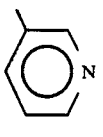 |  | O | O | −CH$_2$CH(CH$_2$CH$_3$)CH$_2$− |
| 114 | 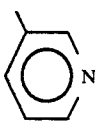 | 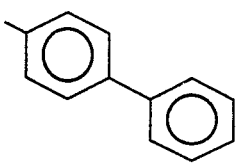 | O | O | −CH$_2$CH(CH$_2$CH$_3$)CH$_2$− |
| 115 | 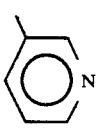 |  | O | O | −CH$_2$CH(CH$_2$CH$_2$CH$_3$)CH$_2$− |
| 116 | 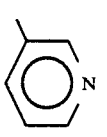 | 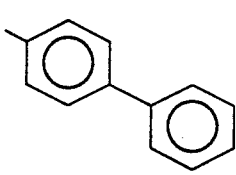 | O | O | −CH$_2$CH(CH$_2$CH$_2$CH$_3$)CH$_2$− |
| 117 | 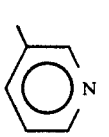 | 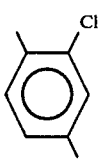 | O | O | −CH$_2$−CH(CH(CH$_3$)$_2$)−CH$_2$− |
| 118 | 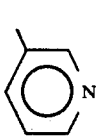 | 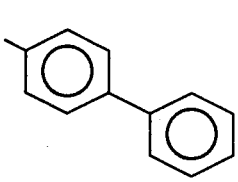 | O | O | −CH$_2$−CH(CH(CH$_3$)$_2$)−CH$_2$− mp. 132–140° C. |
| 119 | 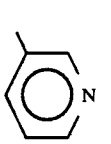 | 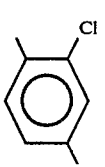 | O | O | −CH$_2$−CH(CH$_2$CH$_2$CH$_2$CH$_3$)−CH$_2$− |
| 120 | 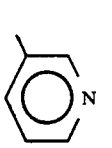 | 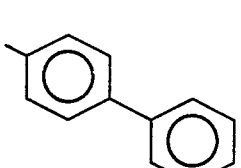 | O | O | −CH$_2$−CH(CH$_2$CH$_2$CH$_2$CH$_3$)−CH$_2$− |

-continued
| | | | | |
|---|---|---|---|---|
| 121 | 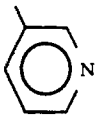 | 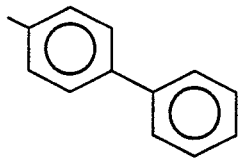 | O  O | −CH$_2$−CH−CH$_2$− with CH$_2$CH(CH$_3$)$_2$ |
| 122 | 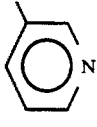 | 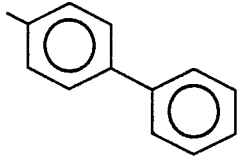 | O  O | −CH$_2$−CH−CH$_2$− with CH$_3$CHCH$_2$CH$_3$ |
| 123 | 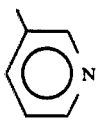 |  | O  O | −CH$_2$−CH−CH$_2$− with C(CH$_3$)$_3$ |
| 124 | 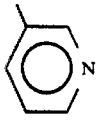 | 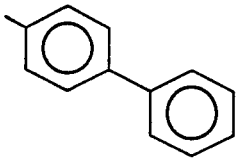 | O  O | −CH$_2$−CH−CH$_2$− with C(CH$_3$)$_3$ |
| 125 |  |  | O  O | −CH$_2$−CH−CH− with CH$_3$ CH$_3$ |
| 126 | 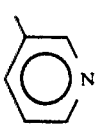 | 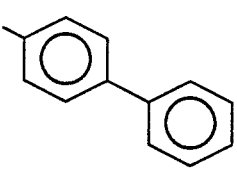 | O  O | −CH$_2$−CH−CH− with CH$_3$ CH$_3$ |
| 127 | 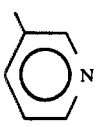 |  | O  O | −CH$_2$−CH−CH− with CH$_3$CH$_2$ CH$_3$ |
| 128 | 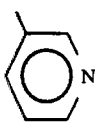 |  | O  O | −CH$_2$−CH−CH− with CH$_3$CH$_2$ CH$_3$ |
| 129 | 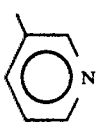 |  | O  O | −CH$_2$−CH−CH− with CH$_3$CH$_2$ CH$_3$ |

| | | | | | |
|---|---|---|---|---|---|
| 130 | 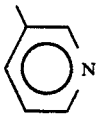 | 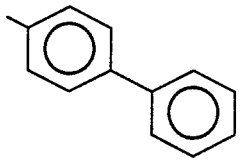 | O O | CH₃CH₂  CH₃<br>    \|     \|<br>—CH₂—CH—CH— | oily |
| 131 | 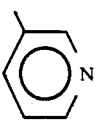 | 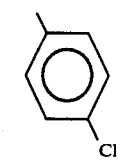 | O O | CH₃CH₂CH₂  CH₃<br>       \|      \|<br>—CH₂—CH—CH— | |
| 132 | 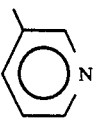 |  | O O | CH₃CH₂CH₂  CH₃<br>       \|      \|<br>—CH₂—CH—CH— | |
| 133 | 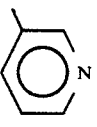 |  | O O | CH₃CH₂CH₂  CH₃<br>       \|      \|<br>—CH₂—CH—CH— | |
| 134 | 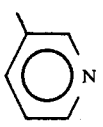 | 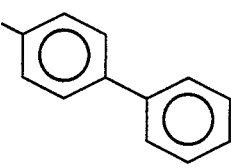 | O O | CH₃CH₂CH₂  CH₃<br>       \|      \|<br>—CH₂—CH—CH— | |
| 135 | 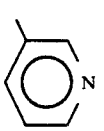 |  | O O | (CH₃)₂CH  CH₃<br>    \|     \|<br>—CH₂—CH—CH— | |
| 136 | 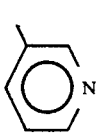 | 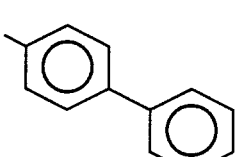 | O O | (CH₃)₂CH  CH₃<br>    \|     \|<br>—CH₂—CH—CH— | |
| 137 | 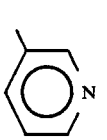 | 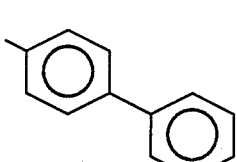 | O O | CH₃CH₂CH₂CH₂  CH₃<br>         \|      \|<br>—CH₂—CH—CH— | |
| 138 | 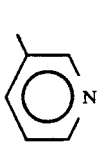 | 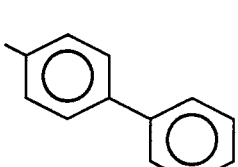 | O O |        CH₃<br>        \|<br>CH₃CH₂CH  CH₃<br>     \|     \|<br>—CH₂—CH—CH— | |

| | | | | |
|---|---|---|---|---|
| 139 | 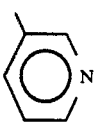 | 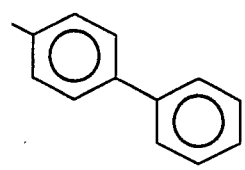 | O O | $\underset{-CH_2-CH-CH-}{(CH_3)_3C \quad CH_3}$ |
| 140 | 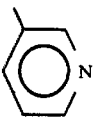 |  | O O | $\underset{-CH_2-CH-CH-}{CH_3 \quad CH_2CH_3}$ |
| 141 | 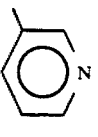 |  | O O | $\underset{-CH_2-CH-CH-}{CH_3 \quad CH_2CH_3}$ |
| 142 | 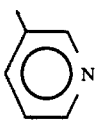 |  | O O | $\underset{-CH_2-CH-CH-}{CH_3 \quad CH_2CH_3}$ |
| 143 | 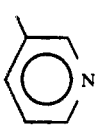 | 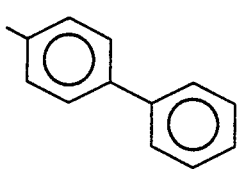 | O O | $\underset{-CH_2-CH-CH-}{CH_3 \quad CH_2CH_3}$ |
| 144 | 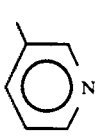 | 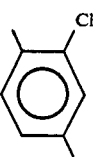 | O O | $\underset{-CH_2-CH-CH-}{CH_3CH_2 \quad CH_2CH_3}$ |
| 145 | 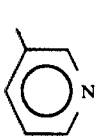 | 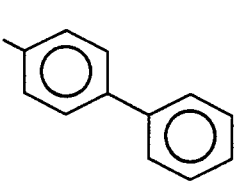 | O O | $\underset{-CH_2-CH-CH-}{CH_3CH_2 \quad CH_2CH_3}$ |
| 146 | 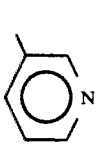 | 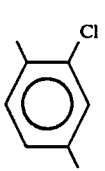 | O O | $\underset{-CH_2-CH-CH-}{CH_3CH_2CH_2 \quad CH_2CH_3}$ |
| 147 | 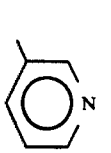 | 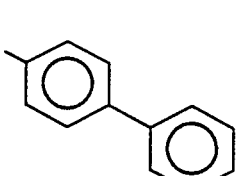 | O O | $\underset{-CH_2-CH-CH-}{CH_3CH_2CH_2 \quad CH_2CH_3}$ |

-continued

| | | | | | |
|---|---|---|---|---|---|
| 148 | 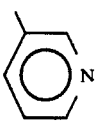 | 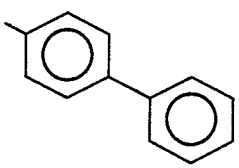 | O | O | $\underset{-CH_2-CH-CH-}{\overset{(CH_3)_2CH\quad CH_2CH_3}{\phantom{X}}}$ |
| 149 | 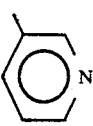 | 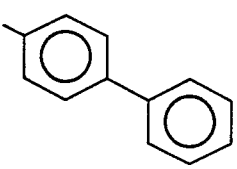 | O | O | $\underset{-CH_2-CH-CH-}{\overset{(CH_3)_3C\quad CH_2CH_3}{\phantom{X}}}$ |
| 150 | 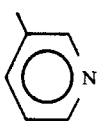 |  | O | O | $\underset{-CH_2-CH-CH-}{\overset{CH_3\quad CH_2CH_2CH_3}{\phantom{X}}}$ |
| 151 | 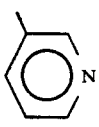 | 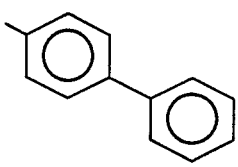 | O | O | $\underset{-CH_2-CH-CH-}{\overset{CH_3\quad CH_2CH_2CH_3}{\phantom{X}}}$ |
| 152 | 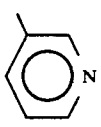 |  | O | O | $\underset{-CH_2-CH-CH-}{\overset{CH_3CH_2\quad CH_2CH_3}{\phantom{X}}}$ |
| 153 | 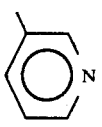 | 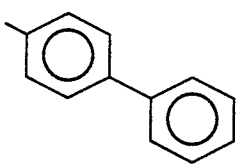 | O | O | $\underset{-CH_2-CH-CH-}{\overset{CH_3CH_2\quad CH_2CH_2CH_3}{\phantom{X}}}$ $n_D^{20}$ 1.5852 |
| 154 | 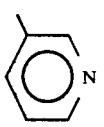 | 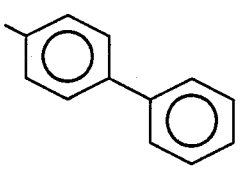 | O | O | $\underset{-CH_2-CH-CH-}{\overset{CH_3CH_2CH_2\quad CH_2CH_2CH_3}{\phantom{X}}}$ |
| 155 | 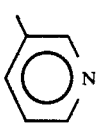 | 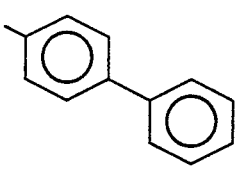 | O | O | $\underset{-CH_2-CH-CH-}{\overset{(CH_3)_2CH\quad CH_2CH_2CH_3}{\phantom{X}}}$ |
| 156 | 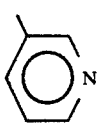 | 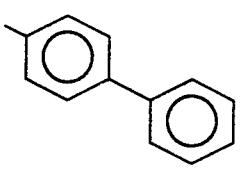 | O | O | $\underset{-CH_2-CH-CH-}{\overset{CH_3CH_2CH_2\quad CH_2CH_2CH_3}{\phantom{X}}}$ |

| | | | | | |
|---|---|---|---|---|---|
| 157 | 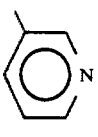 |  | O | O | $-CH_2-\overset{\overset{\displaystyle CH_3}{\mid}}{CH}-\overset{\overset{\displaystyle CH(CH_3)_2}{\mid}}{CH}-$ |
| 158 |  | 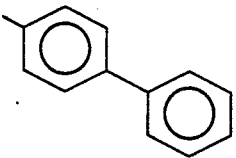 | O | O | $-CH_2-\overset{\overset{\displaystyle CH_3}{\mid}}{CH}-\overset{\overset{\displaystyle CH(CH_3)_2}{\mid}}{CH}-$ |
| 159 |  | 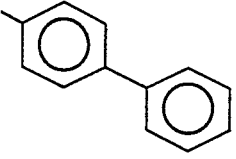 | O | O | $-CH_2-\overset{\overset{\displaystyle CH_3CH_2}{\mid}}{CH}-\overset{\overset{\displaystyle CH(CH_3)_2}{\mid}}{CH}-$ |
| 160 | 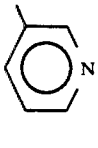 | 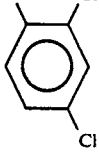 | O | O | $-CH_2-\overset{\overset{\displaystyle CH_3}{\mid}}{CH}-\overset{\overset{\displaystyle CH_2CH_2CH_2CH_3}{\mid}}{CH}-$ |
| 161 | 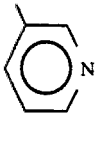 | 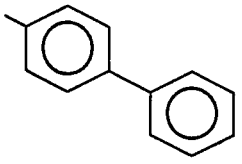 | O | O | $-CH_2-\overset{\overset{\displaystyle CH_3}{\mid}}{CH}-\overset{\overset{\displaystyle CH_2CH_2CH_2CH_3}{\mid}}{CH}-$ |
| 162 | 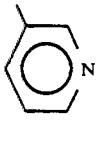 | 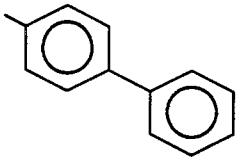 | O | O | $-CH_2-\overset{\overset{\displaystyle CH_3CH_2}{\mid}}{CH}-\overset{\overset{\displaystyle CH_2CH_2CH_3}{\mid}}{CH}-$ |
| 163 | 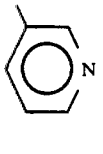 | 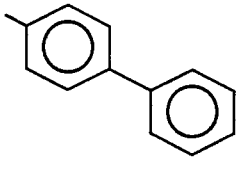 | O | O | $-CH_2-\overset{\overset{\displaystyle CH_3}{\mid}}{CH}-\overset{\overset{\displaystyle \overset{\displaystyle CH_3}{\mid}}{CHCH_2CH_3}}{CH}-$ |
| 164 |  | 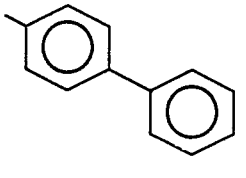 | O | O | $-CH_2-\overset{\overset{\displaystyle CH_3}{\mid}}{CH}-\overset{\overset{\displaystyle C(CH_3)_3}{\mid}}{CH}-$ |
| 165 |  |  | O | O | $-\overset{\overset{\displaystyle CH_3}{\mid}}{CH}-CH_2-\overset{\overset{\displaystyle CH_3}{\mid}}{CH}-$ |

-continued

| | | | | | |
|---|---|---|---|---|---|
| 166 | pyridinyl (methyl) | 4-biphenylyl (methyl) | O | O | -CH(CH₃)-CH₂-CH(CH₃)- | $n_D^{20}$ 1.5967 |
| 167 | pyridinyl (methyl) | 2,4-dichlorophenyl (methyl) | O | O | -CH(CH₃)-CH₂-CH(CH₂CH₃)- | |
| 168 | pyridinyl (methyl) | 4-biphenylyl (methyl) | O | O | -CH(CH₃)-CH₂-CH(CH₂CH₃)- | |
| 169 | pyridinyl (methyl) | 2,4-dichlorophenyl (methyl) | O | O | -CH(CH₃)-CH₂-CH(CH₂CH₂CH₃)- | |
| 170 | pyridinyl (methyl) | 4-biphenylyl (methyl) | O | O | -CH(CH₃)-CH₂-CH(CH₂CH₂CH₃)- | |
| 171 | pyridinyl (methyl) | 2,4-dichlorophenyl (methyl) | O | O | -CH(CH₃)-CH₂-CH(CH(CH₃)₂)- | |
| 172 | pyridinyl (methyl) | 4-biphenylyl (methyl) | O | O | -CH(CH₃)-CH₂-CH(CH(CH₃)₂)- | |
| 173 | pyridinyl (methyl) | 2,4-dichlorophenyl (methyl) | O | O | -CH(CH₃)-CH₂-CH(CH₂CH₂CH₂CH₃)- | |
| 174 | pyridinyl (methyl) | 4-biphenylyl (methyl) | O | O | -CH(CH₃)-CH₂-CH(CH₂CH₂CH₂CH₃)- | |

-continued

| | | | | |
|---|---|---|---|---|
| 175 |  | 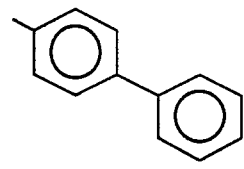 | O O | $-\overset{CH_3}{\underset{}{CH}}-CH_2-\overset{CH_2CH(CH_3)_2}{\underset{}{CH}}-$ |
| 176 | 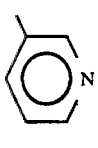 | 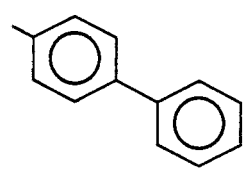 | O O | $-\overset{CH_3}{\underset{}{CH}}-CH_2-\overset{CH_3}{\underset{}{\overset{|}{CH}}}CH_2CH_3 \atop CH-$ |
| 177 | 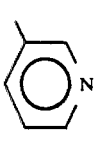 |  | O O | $-\overset{CH_3}{\underset{}{CH}}-CH_2-\overset{C(CH_3)_3}{\underset{}{CH}}-$ |
| 178 | 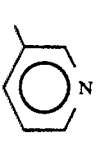 | 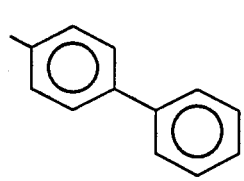 | O O | $-\overset{CH_3}{\underset{}{CH}}-CH_2-\overset{C(CH_3)_3}{\underset{}{CH}}-$ |
| 179 | 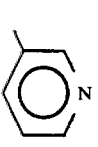 |  | O O | $-\overset{CH_3CH_2}{\underset{}{CH}}-CH_2-\overset{CH_2CH_3}{\underset{}{CH}}-$ |
| 180 | 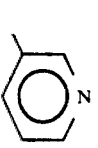 | 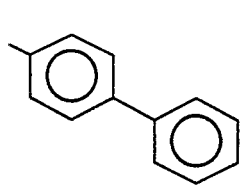 | O O | $-\overset{CH_3CH_2}{\underset{}{CH}}-CH_2-\overset{CH_2CH_3}{\underset{}{CH}}-$ |
| 181 | 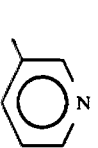 | 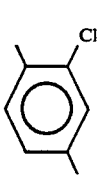 | O O | $-\overset{CH_3CH_2}{\underset{}{CH}}-CH_2-\overset{CH_2CH_2CH_3}{\underset{}{CH}}-$ |
| 182 | 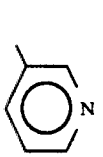 | 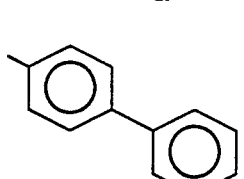 | O O | $-\overset{CH_3CH_2}{\underset{}{CH}}-CH_2-\overset{CH_2CH_2CH_3}{\underset{}{CH}}-$ |
| 183 | 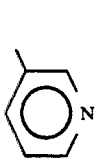 | 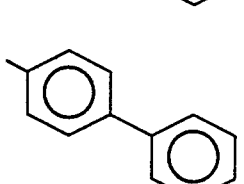 | O O | $-\overset{CH_3CH_2}{\underset{}{CH}}-CH_2-\overset{CH(CH_3)_2}{\underset{}{CH}}-$ |

| | | | | | |
|---|---|---|---|---|---|
| 184 | 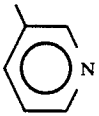 | 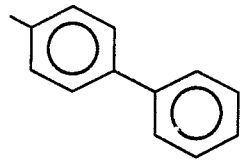 | O | O | CH₃CH₂     CH₂CH₂CH₃<br>—CH—CH₂—CH— |
| 185 | 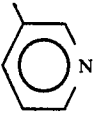 | 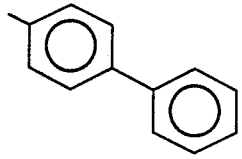 | O | O | CH₃CH₂     C(CH₃)₃<br>—CH—CH₂—CH— |
| 186 | 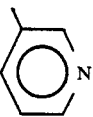 |  | O | O | (CH₃)₃C     C(CH₃)₃<br>—CH—CH₂—CH— |
| 187 | 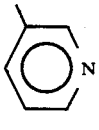 | 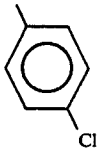 | O | O | CH₃    CH₃<br>—CH—CH—CH—<br>      CH₂CH₃ |
| 188 |  |  | O | O | CH₃    CH₃<br>—CH—CH—CH—<br>      CH₂CH₃ |
| 189 |  | 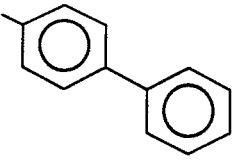 | O | O | CH₃    CH₃<br>—CH—CH—CH—<br>      CH₂CH₃ |
| 190 | 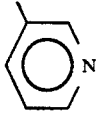 |  | O | O | CH₃ CH₃ CH₃<br>—CH—C—CH—<br>     CH₃ |
| 191 |  | 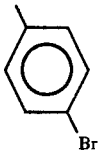 | O | O | CH₃ CH₃ CH₃<br>—CH—C—CH—<br>     CH₃ |
| 192 | 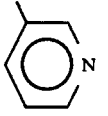 |  | O | O | CH₃ CH₃ CH₃<br>—CH—C—CH—<br>     CH₃ |

-continued
| | | | | | |
|---|---|---|---|---|---|
| 193 | 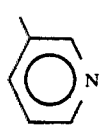 | 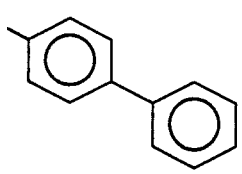 | O O | 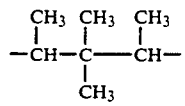 | |
| 194 | 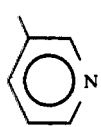 | 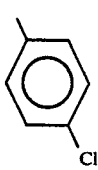 | O O | 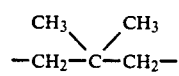 | $n_D^{20}$ 1.5659 |
| 195 | 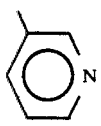 | 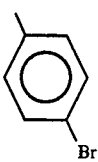 | O O | 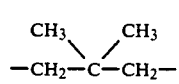 | $n_D^{40}$ 1.5655 |
| 196 | 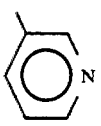 |  | O O | 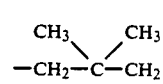 | $n_D^{20}$ 1.5684 |
| 197 | 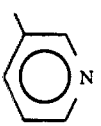 | 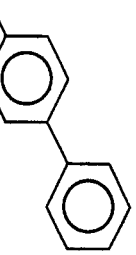 | O O | 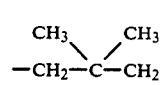 | mp 131–132.5° C. |
| 198 | 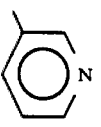 |  | O O | 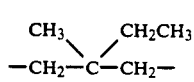 | $n_D^{20}$ 1.5625 |
| 199 |  | 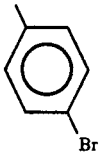 | O O | 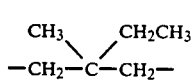 | $n_D^{40}$ 1.5515 |
| 200 | 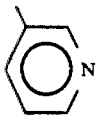 |  | O O | 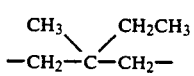 | $n_D^{20}$ 1.5500 |

| | | | | | |
|---|---|---|---|---|---|
| 201 | 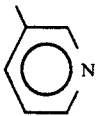 | 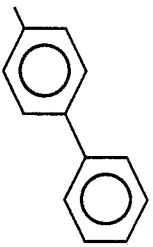 | O O | 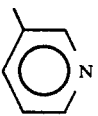 | |
| 202 | 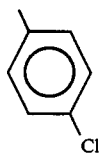 | 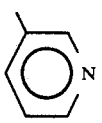 | O O | 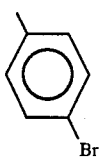 | |
| 203 | 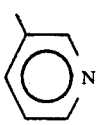 | 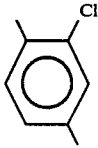 | O O | 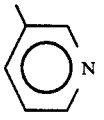 | $n_D^{25}$ 1.5381 |
| 204 | 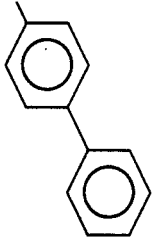 | 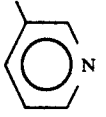 | O O |  | $n_D^{20}$ 1.5528 |
| 205 | 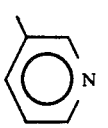 | 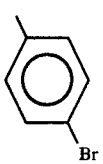 | O O | 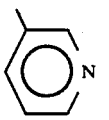 | mp. 118–120° C. |
| 206 | | | O O | | |
| 207 | | | O O | | |
| 208 | | | O O | | |

-continued
| | | | | | |
|---|---|---|---|---|---|
| 209 | 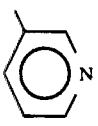 | 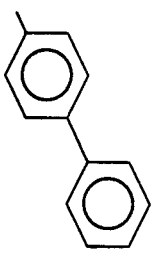 | O | O | 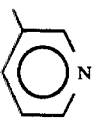 |
| 210 | 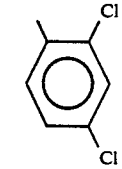 | 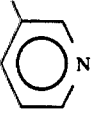 | O | O | 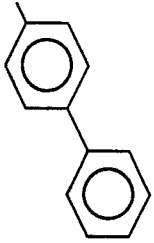 |
| 211 |  | 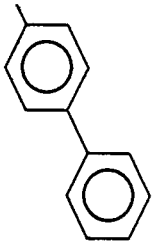 | O | O | 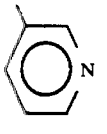 |
| 212 | 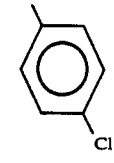 | 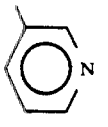 | O | O | 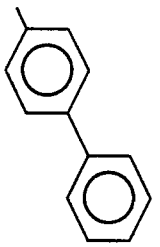 |
| 213 | 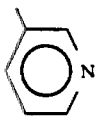 | 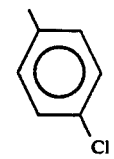 | O | O |  | $n_D^{20}$ 1.5642 |
| 214 | | | O | O | | mp. 125-127° C. |
| 215 | | | O | O | | |

| | | | | | |
|---|---|---|---|---|---|
| 216 | 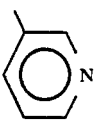 |  | O O | CH$_3$CH$_2$ CH$_2$CH$_3$<br>—CH$_2$—C—CH$_2$— | |
| 217 | 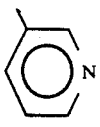 |  | O O | CH$_3$CH$_2$ CH$_2$CH$_3$<br>—CH$_2$—C—CH$_2$— | n$_D^{20}$ 1.5425 |
| 218 | 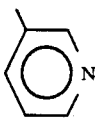 | 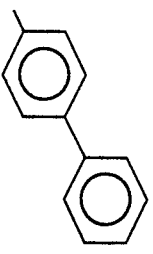 | O O | CH$_3$CH$_2$ CH$_2$CH$_3$<br>—CH$_2$—C—CH$_2$— | mp. 124–125° C. |
| 219 | 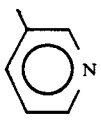 | 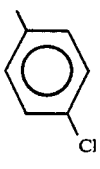 | O O | CH$_3$CH$_2$ CH(CH$_3$)$_2$<br>—CH$_2$—C—CH$_2$— | |
| 220 |  |  | O O | CH$_3$CH$_2$ CH(CH$_3$)$_2$<br>—CH$_2$—C—CH$_2$— | n$_D^{50}$ 1.5520 |
| 221 |  | 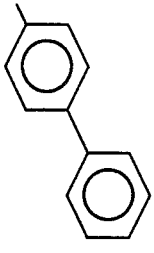 | O O | CH$_3$CH$_2$ CH(CH$_3$)$_2$<br>—CH$_2$—C—CH$_2$— | |
| 222 | 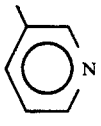 |  | O O | CH$_3$CH$_2$ CH$_2$CH$_2$CH$_3$<br>—CH$_2$—C—CH$_2$— | |
| 223 | 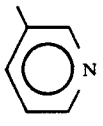 | 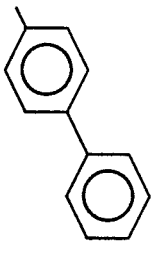 | O O | CH$_3$CH$_2$ CH$_2$CH$_2$CH$_3$<br>—CH$_2$—C—CH$_2$— | |

-continued
| | | | | | |
|---|---|---|---|---|---|
| 224 | 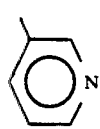 | 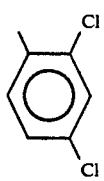 | O | O | 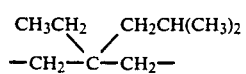 |
| 225 | 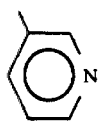 | 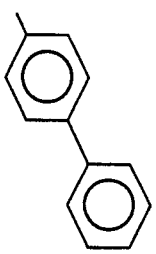 | O | O | 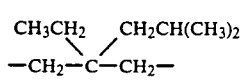 |
| 226 | 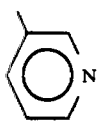 |  | O | O | 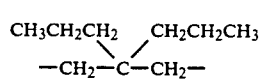 |
| 227 | 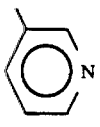 | 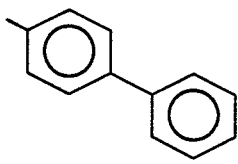 | O | O | 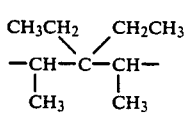 |
| 228 | 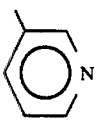 |  | S | O |  |
| 229 | 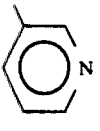 | 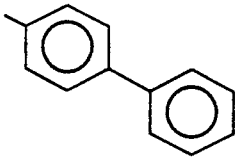 | S | O | 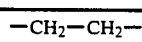 |
| 230 | 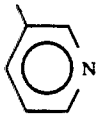 |  | S | O | 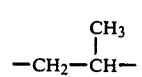 |
| 231 |  | 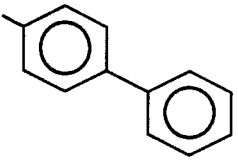 | S | O | 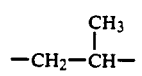 |

-continued
| | | | | | |
|---|---|---|---|---|---|
| 232 |  |  | S | O | 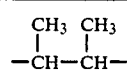 |
| 233 | 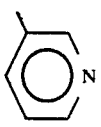 | 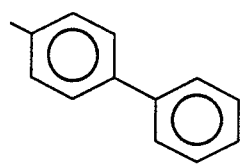 | S | O | 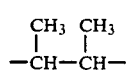 |
| 234 | 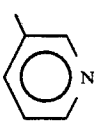 |  | S |  | 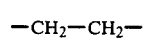 |
| 235 | 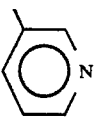 | 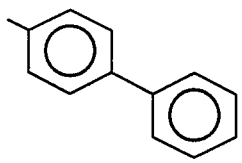 | S |  | 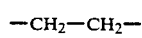 |
| 236 | 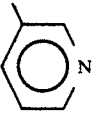 |  | S |  | 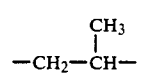 |
| 237 | 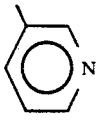 |  | O | O | 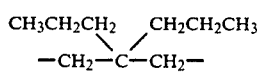 $n_D^{20}$ 1.5480 |
| 238 | 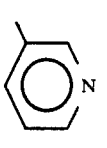 |  | O | O | 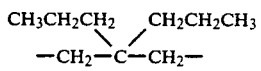 $n_D^{20}$ 1.5450 |
| 239 | 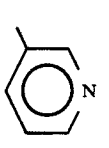 | 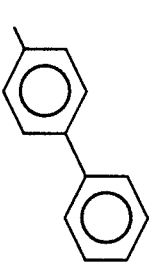 | O | O | 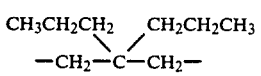 mp. 135–136° C. |

| | | | | | |
|---|---|---|---|---|---|
| 240 | 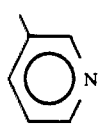 | 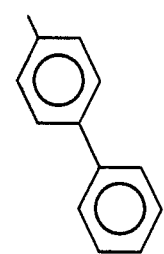 | O | O | CH₃CH₂ CH(CH₃)₂<br>—CH₂—C—CH₂— |
| 241 | 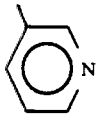 | 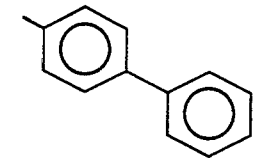 | O | O | CH₃CH₂CH₂ CH₂CH₂CH₃<br>—CH₂—C—CH₂— |
| 242 | 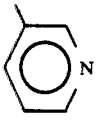 | 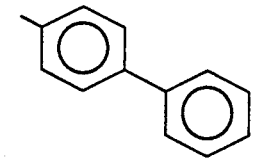 | O | O | CH₃ CH₃ CH₃<br>—CH—C—CH—<br>CH(CH₃)₂ |
| 243 | 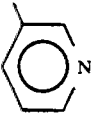 | 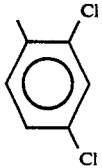 | O | O | CH₃CH₂ CH₂CH₃<br>—CH—C—CH—<br>CH₃ CH₃ |
| 244 | 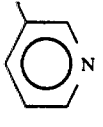 |  | S | S | CH₃<br>—CH₂—CH— | oily |
| 245 | 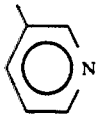 | 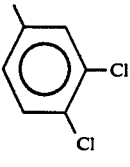 | S | S | CH₃<br>—CH₂—CH— |
| 246 | 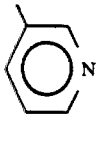 | 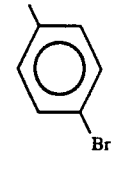 | S | S | —CH₂—CH₂— |
| 247 | 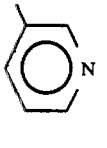 | 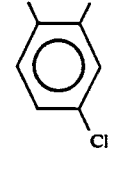 | S | S | —CH₂—CH₂— |

| | | | | |
|---|---|---|---|---|
| 248 | 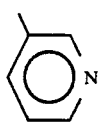 | 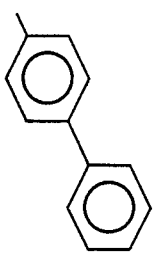 | S  S | —CH₂—CH₂— |
| 249 | 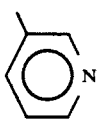 | 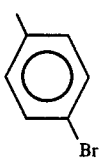 | S  S | —CH₂—CH(CH₃)— |
| 250 | 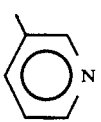 | 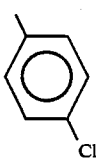 | S  S | —CH₂—CH(CH₂CH₃)— |
| 251 | 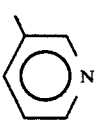 | 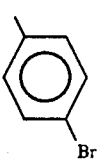 | S  S | —CH₂—CH(CH₂CH₃)— |
| 252 |  | 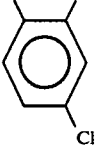 | S  S | —CH₂—CH(CH₂CH₃)— |
| 253 | 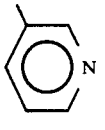 | 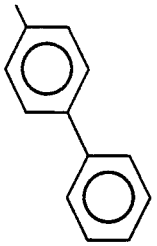 | S  S | —CH₂—CH(CH₂CH₃)— |
| 254 | 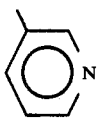 | 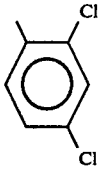 | S  S | —CH₂—CH(CH₂CH₂CH₃)— |
| 255 | 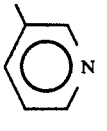 | 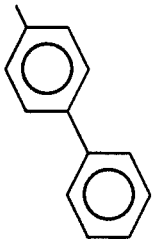 | S  S | —CH₂—CH(CH₂CH₂CH₃)— |

-continued
| | | | | | |
|---|---|---|---|---|---|
| 256 | 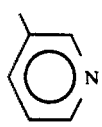 |  | S | S | 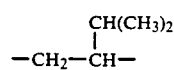 |
| 257 | 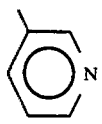 | 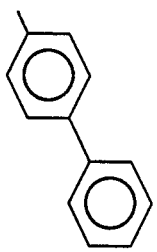 | S | S | 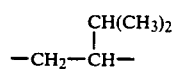 |
| 258 | 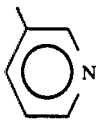 |  | S | S | 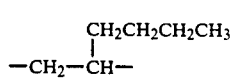 |
| 259 | 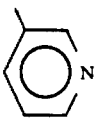 | 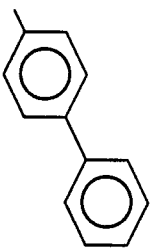 | S | S | 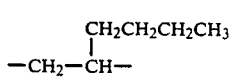 |
| 260 | 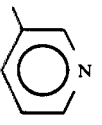 | 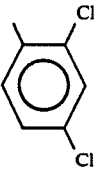 | S | S | 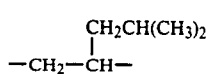 |
| 261 | 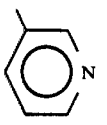 | 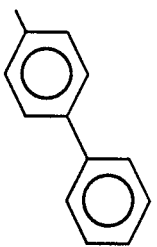 | S | S | 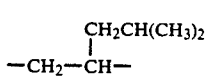 |
| 262 | 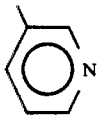 |  | S | S | 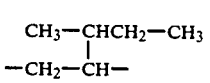 |

-continued
| | | | | |
|---|---|---|---|---|
| 263 | 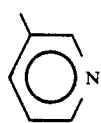 | 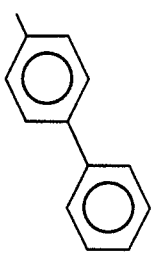 | S  S | CH₃—CHCH₂CH₃<br>—CH₂—CH— |
| 264 | 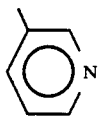 |  | S  S | C(CH₃)₃<br>—CH₂CH— |
| 265 | 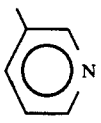 | 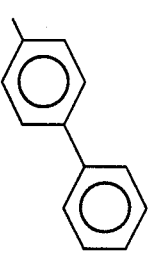 | S  S | C(CH₃)₃<br>—CH₂CH— |
| 266 | 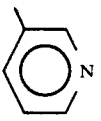 |  | S  S | CH₂Cl<br>—CH₂CH— |
| 267 | 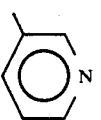 | 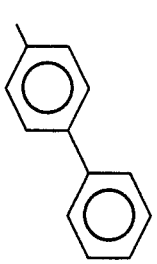 | S  S | CH₂Cl<br>—CH₂CH— |
| 268 | 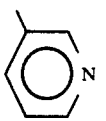 |  | S  S | CH₂OCH₃<br>—CH₂CH— |
| 269 |  | 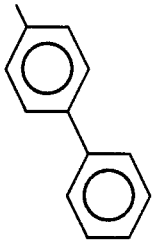 | S  S | CH₂OCH₃<br>—CH₂CH— |

-continued
| | | | | |
|---|---|---|---|---|
| 270 | 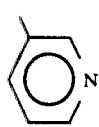 |  | S  S | 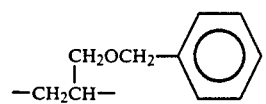 |
| 271 |  | 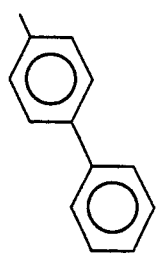 | S  S | 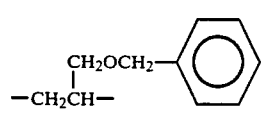 |
| 272 | 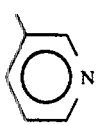 |  | S  S | 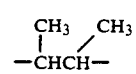 |
| 273 | 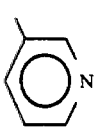 | 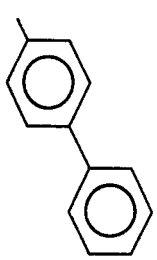 | S  S | 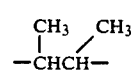 |
| 274 | 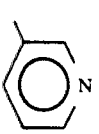 | 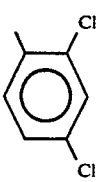 | S  S | 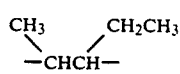 |
| 275 | 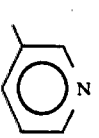 | 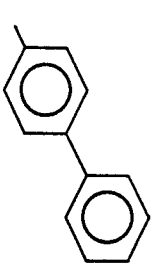 | S  S | 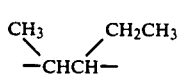 |
| 276 | 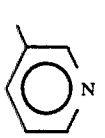 |  | S  S | 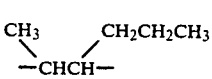 |

-continued
| | | | | |
|---|---|---|---|---|
| 277 | 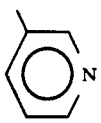 | 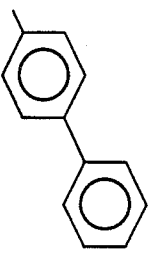 | S  S | 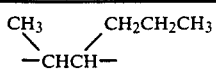 |
| 278 | 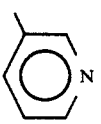 |  | S  S | 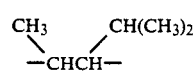 |
| 279 | 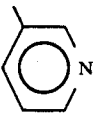 | 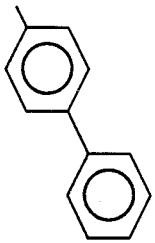 | S  S | 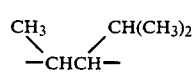 |
| 280 | 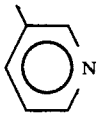 |  | S  S | 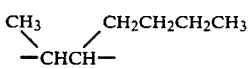 |
| 281 | 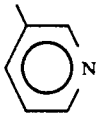 | 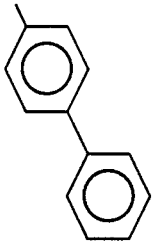 | S  S | 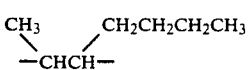 |
| 282 | 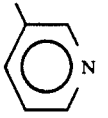 |  | S  S | 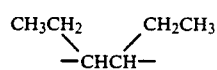 |
| 283 | 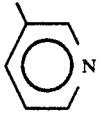 | 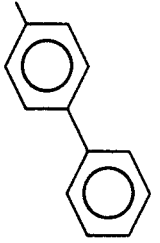 | S  S | 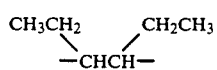 |

-continued
| | | | | | |
|---|---|---|---|---|---|
| 284 | 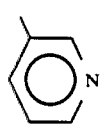 | 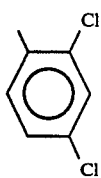 | S | S | 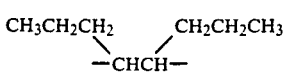 |
| 285 | 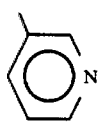 | 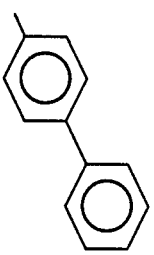 | S | S | 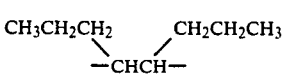 |
| 286 | 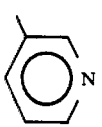 |  | S | S | 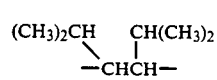 |
| 287 | 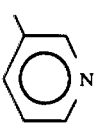 | 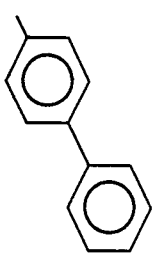 | S | S | 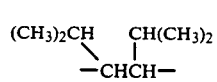 |
| 288 | 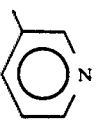 | 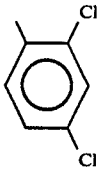 | S | S | 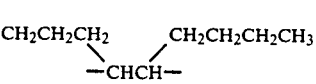 |
| 289 | 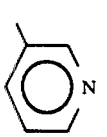 | 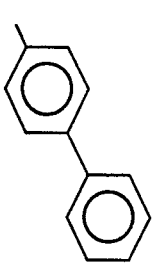 | S | S | 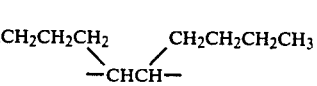 |
| 290 | 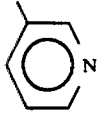 |  | S | S | 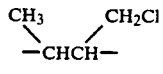 |

-continued
| | | | | |
|---|---|---|---|---|
| 291 | 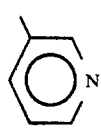 |  | S S | —CH₂CH₂CH₂— |
| 292 | 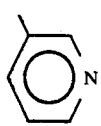 | 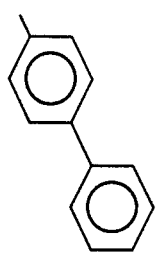 | S S | —CH₂CH₂CH₂— |
| 293 | 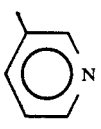 | 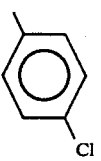 | S S | 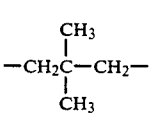 |
| 294 | 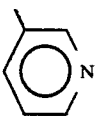 |  | S S | 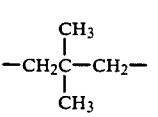 |
| 295 | 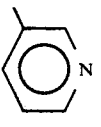 | 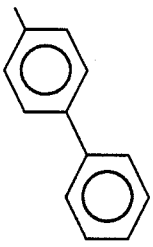 | S S | 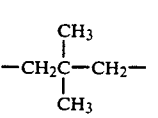 |
| 296 | 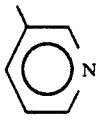 | 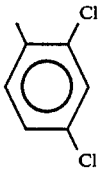 | O O | 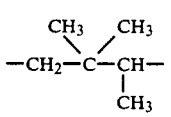 |
| 297 | 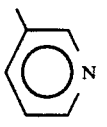 | 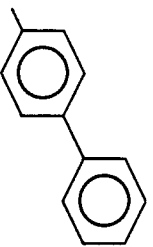 | O O | 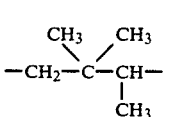 |
| 298 | 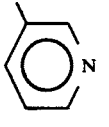 |  | O O | 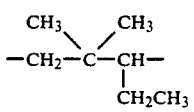 |

-continued
| | | | | |
|---|---|---|---|---|
| 299 | 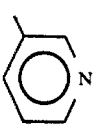 | 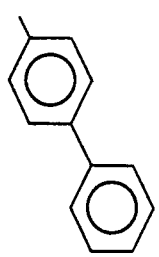 | O  O | 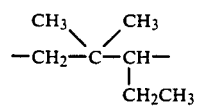 |
| 300 | 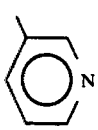 |  | O  O | 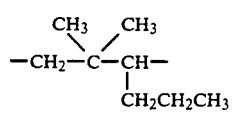 |
| 301 | 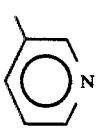 | 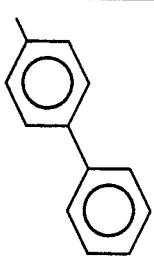 | O  O | 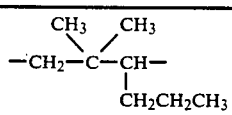 |
| 302 | 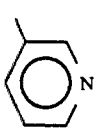 |  | O  O | 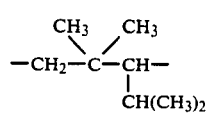 |
| 303 | 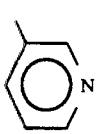 | 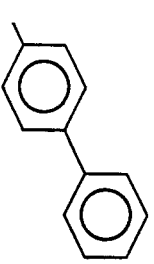 | O  O | 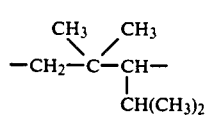 |
| 304 | 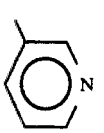 |  | O  O | 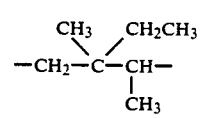 |
| 305 | 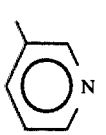 | 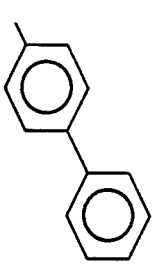 | O  O | 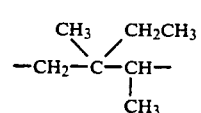 |

| | | | | |
|---|---|---|---|---|
| 306 | 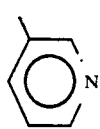 | 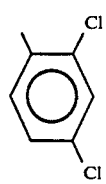 O O | 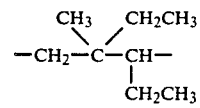 |
| 307 | 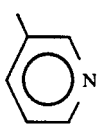 | 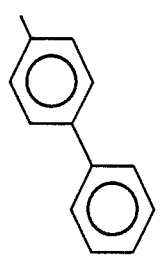 O O | 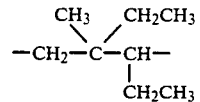 |
| 308 | 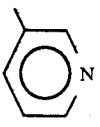 |  O O | 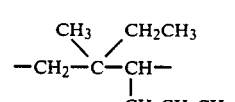 |
| 309 | 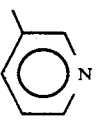 | 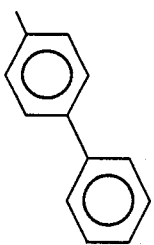 O O | 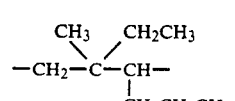 |
| 310 | 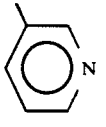 |  O O | 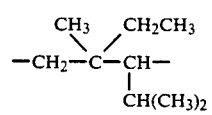 |
| 311 | 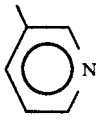 | 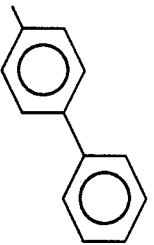 O O | 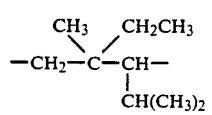 |
| 312 | 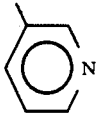 |  O O | 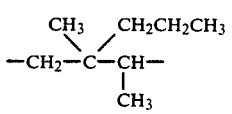 |

| | | | | |
|---|---|---|---|---|
| 313 | 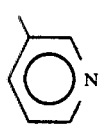 | 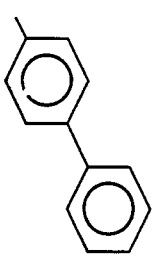 | O O | 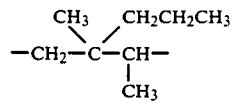 |
| 314 | 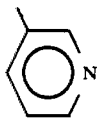 | 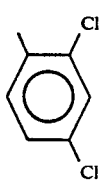 | O O | 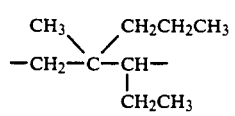 |
| 315 | 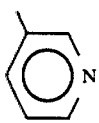 | 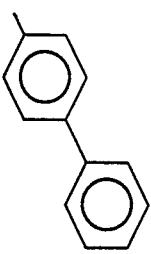 | O O | 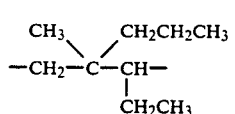 |
| 316 | 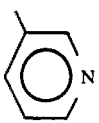 | 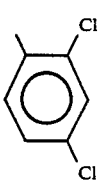 | O O | 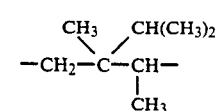 |
| 317 | 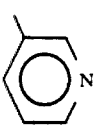 | 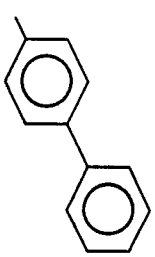 | O O | 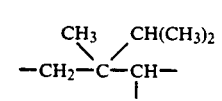 |
| 318 | 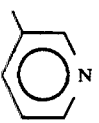 |  | O O | 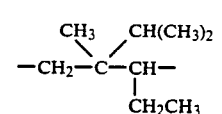 |
| 319 | 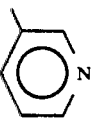 | 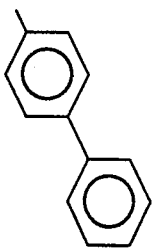 | O O | 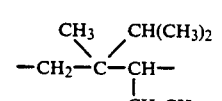 |

-continued
| | | | | |
|---|---|---|---|---|
| 320 | 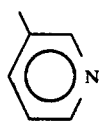 |  | O O | 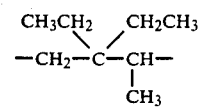 |
| 321 | 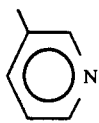 | 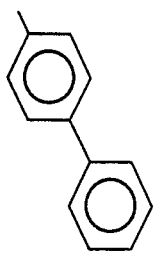 | O O | 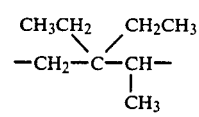 |
| 322 | 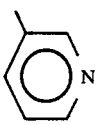 |  | O O | 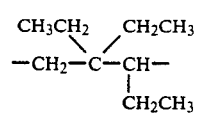 |
| 323 | 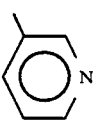 | 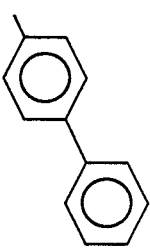 | O O | 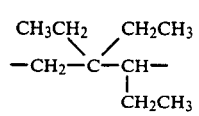 |
| 324 | 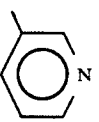 |  | O O | 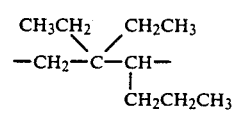 |
| 325 | 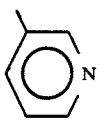 | 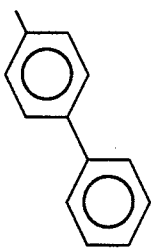 | O O | 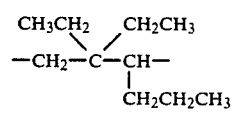 |
| 326 | 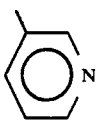 |  | O O | 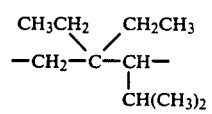 |

| | | | | |
|---|---|---|---|---|
| 327 | 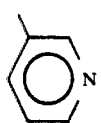 | 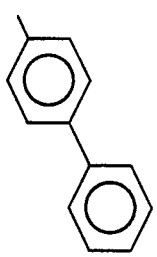 | O O | 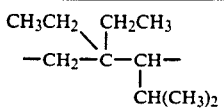 |
| 328 | 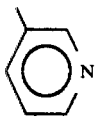 | 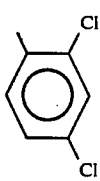 | O O | 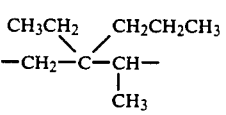 |
| 329 | 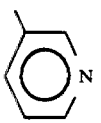 | 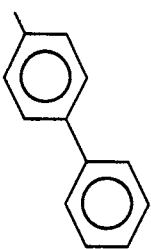 | O O | 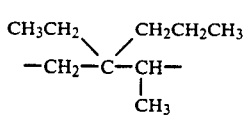 |
| 330 | 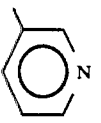 |  | O O | 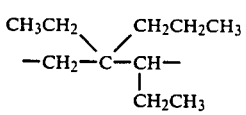 |
| 331 | 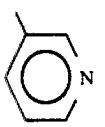 | 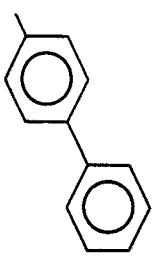 | O O | 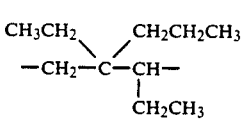 |
| 332 | 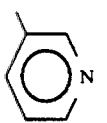 | 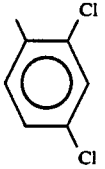 | O O | 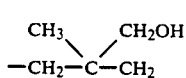 |
| 333 | 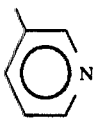 | 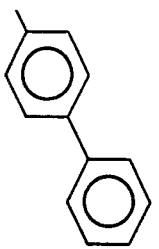 | O O | 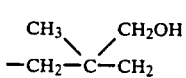 |

| | | | | | |
|---|---|---|---|---|---|
| 334 | 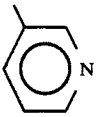 |  | O | O | 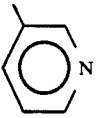 |
| 335 | 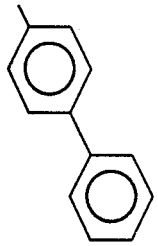 | 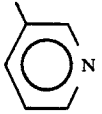 | O | O |  |
| 336 | 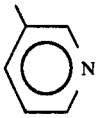 |  | O | O | 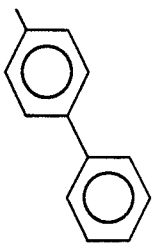 |
| 337 | 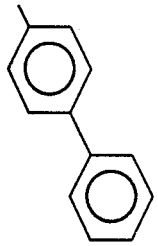 | 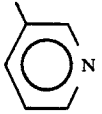 | O | O | 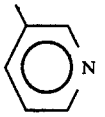 |
| 338 | 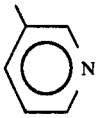 |  | O | O |  |
| 339 | 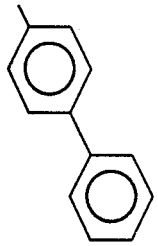 | 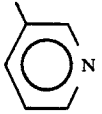 | O | O | 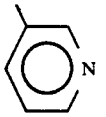 |
| 340 | 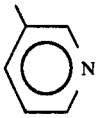 |  | O | O | 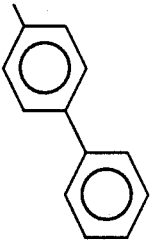 |
| 341 | 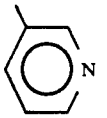 |  | S | S | 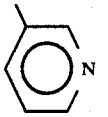 | $n_D^{20}$ 1.6230 |

| | | | | | |
|---|---|---|---|---|---|
| 342 | 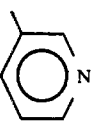 |  | O O | —CH₂CH₂CH₂— | mp. 70-73° C. |
| 343 | 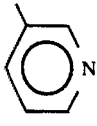 |  | O O | $\underset{}{-CH_2\overset{CH_3}{\underset{|}{CH}}CH_2-}$ | $n_D^{20}$ 1.5550 |
| 344 |  |  | O O | $-CH_2\overset{CH_2CH_3}{\underset{|}{CH}}CH_2-$ | $n_D^{20}$ 1.5477 |
| 345 |  |  | O O | $-CH_2\overset{CH_3}{\underset{\underset{CH_3}{|}}{C}}CH_2-$ | $n_D^{25}$ 1.5419 |
| 346 |  | 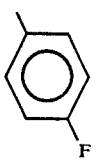 | O O | $-CH_2\overset{CH_3}{\underset{\underset{CH_2CH_3}{|}}{C}}CH_2-$ | $n_D^{25}$ 1.5389 |
| 347 | 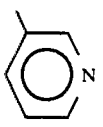 |  | O O | $-CH_2\overset{CH_2CH_3}{\underset{\underset{CH_2CH_3}{|}}{C}}CH_2-$ | $n_D^{25}$ 1.5331 |
| 348 | 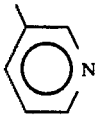 |  | O O | $-CH_2\overset{CH_3}{\underset{\underset{CH_2CH_2CH_3}{|}}{C}}CH_2-$ | $n_D^{20}$ 1.5360 |
| 349 | 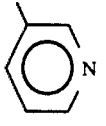 |  | O O | $-CH_2\overset{CH_2CH_2CH_3}{\underset{\underset{CH_2CH_2CH_3}{|}}{C}}CH_2-$ | mp. 91-93.5° C. |
| 350 | 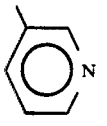 |  | S S | $-CH_2\overset{CH_3}{\underset{|}{CH}}-$ | $n_D^{20}$ 1.6064 |

| | | | | | |
|---|---|---|---|---|---|
| 351 | 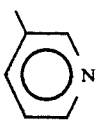 |  | O  O | $-CH_2-\underset{\underset{CH_3}{\mid}}{\overset{\overset{CH_3}{\mid}}{C}}-CH_2-$ | $n_D^{20}$ 1.5330 |
| 352 | 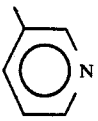 |  | O  O | $-CH_2-\underset{\underset{CH_2CH_3}{\mid}}{\overset{\overset{CH_2CH_3}{\mid}}{C}}-CH_2-$ | $n_D^{20}$ 1.5228 |
| 353 | 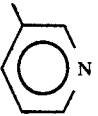 |  | O  O | $-CH_2CH_2CH_2-$ | mp. 77–80° C. |
| 354 | 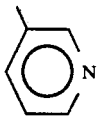 | 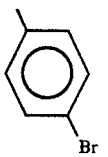 | O  O | $-CH_2\underset{\underset{CH_2CH_3}{\mid}}{CH}CH_2-$ | $n_D^{20}$ 1.5627 |
| 355 | 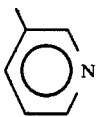 |  | O  O | $-CH_2-\underset{\underset{CH_2CH_3}{\mid}}{\overset{\overset{CH(CH_3)_2}{\mid}}{C}}-CH_2-$ | $n_D^{20}$ 1.5436 |
| 356 | 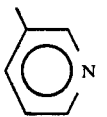 |  | S  S | $-CH_2\underset{\underset{CH_3}{\mid}}{CH}-$ | $n_D^{20}$ 1.6421 |
| 357 | 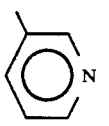 |  | O  O | $-CH_2\underset{\underset{CH_3}{\mid}}{\overset{\overset{CH_3}{\mid}}{C}}CH_2-$ | $n_D^{50}$ 1.5824 |
| 358 | 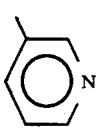 |  | O  O | $-CH_2\underset{\underset{CH_2CH_3}{\mid}}{\overset{\overset{CH_2CH_3}{\mid}}{C}}CH_2-$ | $n_D^{50}$ 1.5600 |
| 359 | 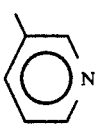 |  | O  O | $-CH_2CH_2CH_2-$ | $n_D^{20}$ 1.5760 |

-continued
| | | | | | | |
|---|---|---|---|---|---|---|
| 360 | 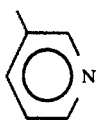 |  | O | O | −CH₂CHCH₂−<br>    \|<br>   CH₃ | $n_D^{20}$ 1.5692 |
| 361 | 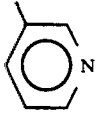 | 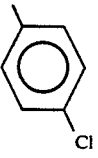 | O | O | CH₂OH<br>  \|<br>−CH₂CH−CH₂−<br>        \|<br>       CH₂OH | $n_D^{20}$ 1.5830 |
| 362 | 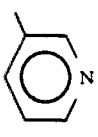 | 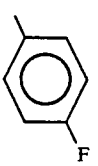 | S | S | −CH₂CH₂− | $n_D^{20}$ 1.6380 |
| 363 |  |  | S | S | −CH₂CH₂− | mp. 54–58° C. |
| 364 | 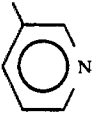 |  | O | O | −CH₂CH₂CH₂− | $n_D^{20}$ 1.5493 |
| 365 |  | 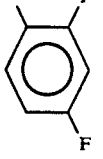 | O | O | −CH₂CHCH₂−<br>    \|<br>   CH₃ | $n_D^{20}$ 1.5354 |
| 366 | 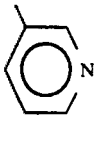 |  | O | O | CH₂CH₃<br>  \|<br>−CH₂C−CH₂−<br>  \| | $n_D^{20}$ 1.5309 |
| 367 | 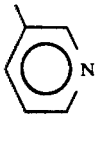 | 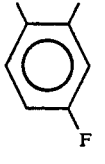 | O | O | CH₃<br>  \|<br>−CH₂C−CH₂−<br>  \|<br>CH₂CH₃ | $n_D^{20}$ 1.5225 |
| 368 | 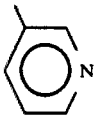 |  | O | O | CH₃<br>  \|<br>−CH₂C−CH₂−<br>  \|<br>CH₂CH₂CH₃ | $n_D^{20}$ 1.5290 |

| 369 | 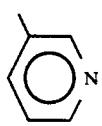 |  | 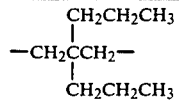 |
|---|---|---|---|

Example 6: Preparation of Intermediate

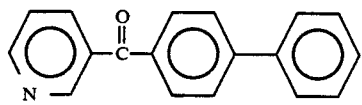

To a suspension of 17.8 g of nicotinyl chloride hydrochloride, 38.2 g of diphenyl and 100 ml of chlorobenzene, 33.3 g of aluminum chloride was added under ice-cooling and the resulting mixture was heated under reflux for six hours. After cooling, the reaction mixture was poured into a solution of ice/hydrochloric acid and washed with chloroform. The aqueous layer was made alkaline with aqueous sodium hydroxide solution and extracted with chloroform. The organic layer was washed with water and dried over anhydrous sodium sulfate. After removal of the sodium sulfate, the solvent was removed under reduced pressure to give 9.1 g of 3-(4-phenylbenzoyl)-pyridine, mp. 112°-115° C.

Example 7: Preparation of Intermediate

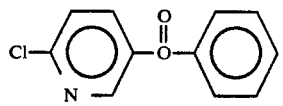

To 40 ml of a solution of 5.28 g of 6-chloronicotinoyl chloride in benzene, 16 g of aluminum chloride was added under ice-cooling and the resulting mixture was heated under reflux for six hours. After cooling, the reaction mixture was poured into a solution of ice/hydrochloric acid and extracted with ether. The organic phase was washed with water and dried over anhydrous sodium sulfate. After filtering off the sodium sulfate and distilling off the solvent, 4.6 g of 3-benzoyl-6-chloropyridine was obtained. m.p.: 39°-40° C.

The following compounds can be prepared by the same method as described above:

3-benzoyl-5-chloropyridine

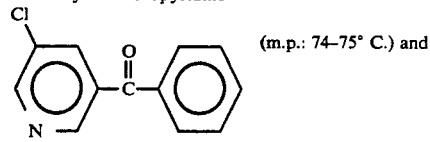 (m.p.: 74–75° C.) and 3-benzoyl-5,6-dichloropyridine

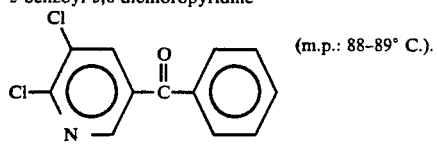 (m.p.: 88–89° C.).

Biotest Examples

Known comparison compounds employed:

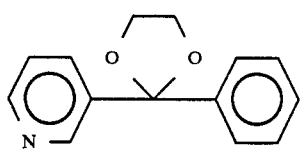 E-1

(Bull. Soc. Chem. Belg. vol. 89, page 67 (1980))

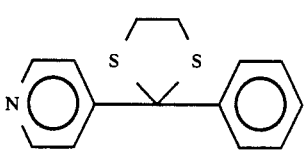 E-2

(J. Chem. Soc. Perkin Trans. I 1984, page 1223)

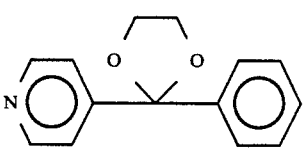 E-3

(Heterocycles, vol. 22, page 1137 (1984))

Example 8

Activity test against Helminthosporium leaf spot (active compounds were sprayed onto leaves and stalks)

Formulation of Active Compounds
Compound to be tested: 30 parts
Organic solvent (xylene): 55 parts
Emulsifier:
  Polyoxyethylenealkylphenyl ether 8 parts
  Calcium alkylbenzenesulfonate 7 parts The prescribed dosage of the emulsion obtained above is prepared by dilution with water.

Test Procedures

Rice plants (Kusabue Variety) were grown in porcelain pots each having a diameter of 12 cm. The rice plants, at the 3–4 leaf stage, were sprayed with the preparation of active compound in an amount of 50 ml per 3 pots. On the next day, the plants were sprayed two times with a suspension of spores of the Gomahagarebyo-causing fungus which had been artificially grown and kept in a moisture chamber at 25° C. and 100% relative humidity for 24 hours. After the artifical inoculation, the plants were placed in the greenhouse at 22°-30° C.

Seven days after the inoculation, the infection of the rice plants was determined and recorded according to the following assessment scale:

| Infection Rating | Infection Degree |
|---|---|
| 0 | non |
| 1 | very slight |

-continued

| Infection Rating | Infection Degree |
|---|---|
| 2 | slight |
| 3 | medium |
| 4 | great |
| 5 | serious |

The percent protection was calculated employing the following equation:

$$\text{Protection (\%)} = \frac{A - B}{A} \times 100$$

wherein

A represents the average infection degree in the control (untreated) pots: and

B represents the average infection degree in the treated pots.

The results of this test are given in Table 2.

TABLE 2

| Compound No. | Active ingredient concentration (ppm) | Protection (%) |
|---|---|---|
| 1 | 500 | 100 |
| 2 | 500 | 100 |
| 3 | 500 | 100 |
| 10 | 500 | 100 |
| 16 | 500 | 100 |
| 17 | 500 | 100 |
| 19 | 500 | 100 |
| 20 | 500 | 100 |
| 22 | 500 | 100 |
| 31 | 500 | 100 |
| 32 | 500 | 100 |
| 35 | 500 | 100 |
| 37 | 500 | 100 |
| 41 | 500 | 100 |
| Comparison | | |
| E-1 | 500 | 47 |
| E-2 | 500 | 60 |
| E-3 | 500 | 43 |

Example 9

Controlling test for powdery mildew on cucumber

Test Procedure

A test compound in the form of emulsion, which was prepared in accordance with Example 8, was sprayed by using a spray gun on a cucumber plant (variety: Tokiwajibai) at 2-leaf stage true leaf cultured in a porous pot 9 cm in diameter. One day after the spraying, the suspension of spore of the pathogen (Sphaerotheca fuliginea) was inoculated by spraying. After leaving in a thermostable chamber at 23° C., the degree of infection was determined based on the rate of lesion area on the 10th day to calculate the controlling effect.

| Infection degree | Rate of lesion area (%) |
|---|---|
| 0 | 0 |
| 0.5 | less than 2 |
| 1 | 3–5 |
| 2 | 6–15 |
| 3 | 16–30 |
| 4 | 31–50 |
| 5 | more than 51 |

$$\text{Control value (\%)} = \frac{\left(\begin{array}{c}\text{infection}\\\text{degree in}\\\text{untreated pot}\end{array}\right) - \left(\begin{array}{c}\text{infection}\\\text{degree in}\\\text{treated pot}\end{array}\right)}{\text{infection degree in untreated pot}} \times 100$$

The results of this test are given in Table 3.

TABLE 3

| Compound No. | Active ingredient concentration (ppm) | Protection (%) |
|---|---|---|
| 42 | 100 | 100 |
| 57 | 100 | 100 |
| 58 | 100 | 100 |
| 60 | 100 | 100 |
| 75 | 100 | 100 |
| 100 | 100 | 100 |
| 130 | 100 | 100 |
| 194 | 100 | 100 |
| 196 | 100 | 100 |
| 200 | 100 | 100 |
| 213 | 100 | 100 |
| 214 | 100 | 100 |
| Comparison | | |
| E-1 | 100 | 20 |

Example 10:

Herbicidal test/water surface treatment/weeds in locations where rice plants are grown under irrigation Formulation of Active Compounds Carrier: 5 parts by weight of acetone Emulsifier: 1 part by weight of benzyloxy polyglycol ether To produce a suitable preparation of active compound, 1 part by weight of active compound was mixed with the stated amount of carrier and with the stated amount of emulsifier, and the resulting emulsifiable concentrate was then diluted with water to the desired concentration.

Test Procedure

Each of several pots, each having a size of 25×20×9 cm and an area of 1/2,000 are, was filled with soil taken from a paddy field. Rice-seedlings (Nihonbare Variety) of the 2.5-leaf stage, with an average height of 15 cm, were transplanted into these pots. Each pot has two zones each including one stock consisting of three plants. Then, seeds of the following weeds were sown in each of the pots, which was kept under wet conditions:

barnyard grass (Echinochloa);

flatsedge (Cyperus);

monochoria (Monochoria); and annual broad-leaved weeds such as false pimpernel (Lindernia), toothcup (Rotala), waterstarwort (Elatine), red stem (Ammannia) and dopatrium (Dopatrium).

After 2 days, water was supplied into each of the pots up to 2–3 cm in depth.

Five days after the transplantation of the rice seedlings, the emulsion of the active compound, which had been prepared in the manner mentioned above, was applied to each of the pots in a predetermined amount by means of a pipette. After that, the water sheet was kept in a thickness of about 3 cm.

Four weeks after the application of the active compound, the degree of damage to the weeds and the degree of phytotoxicity on the rice plants were determined, and recorded according to the following assessment scale:

| Rating | Herbicidal effect of active compound on weeds in %* |
|---|---|
| 5 | 95% or more (fatal effect) |
| 4 | at least 80% and less than 95% |
| 3 | at least 50% and less than 80% |
| 2 | at least 30% and less than 50% |

| Rating | Phytotoxic effect of active compound on crops in %* |
|---|---|
| 1 | at least 10% and less than 30% |
| 0 | less than 10% (no effect) |

| Rating | Phytotoxic effect of active compound on crops in %* |
|---|---|
| 5 | at least 90% (fatal phytotoxicity) |
| 4 | at least 50% and less than 90% |
| 3 | at least 30% and less than 50% |
| 2 | at least 10% and less than 30% |
| 1 | more than 0% and less than 10% |
| 0 | 0% (no phytotoxicity) |

*These values (%) are those obtained by comparing the test data in the treated plant section with the test data in the control (untreated) plant section.

The test results are shown in Table 4.

TABLE 4

| compound | Amount of active compound (kg/ha) | Barnyard grass | Spikerush, Slender (Eleocharis) | Flat sedge | Monochoria | Annual broad-leaved weeds | Phytotoxic effect on rice plants |
|---|---|---|---|---|---|---|---|
| 1 | 2 | 3 | 5 | 4 | 5 | 5 | 0 |
| 2 | 2 | 5 | 5 | 5 | 5 | 5 | 0 |
| 12 | 2 | 4 | 5 | 5 | 5 | 5 | 0 |
| 19 | 2 | 5 | 5 | 5 | 5 | 5 | 0 |
| 32 | 2 | 5 | 5 | 5 | 5 | 5 | 0 |
| Comparison | | | | | | | |
| E-2 | 2 | 0 | 0 | 0 | 0 | 0 | 0 |
| E-3 | 2 | 0 | 0 | 0 | 0 | 0 | 0 |

It will be appreciated that the instant specification and claims are set forth by way of illustration and not limitation, and that various modifications and changes may be made without departing from the spirit and scope of the present invention.

What is claimed is:

1. A 3-substituted pyridine of the formula

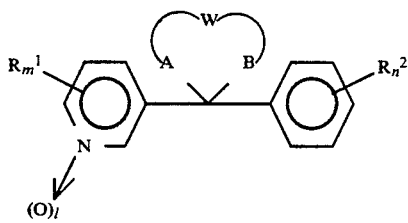

wherein
$R^1$ represents hydrogen, halogen, lower alkyl, or halo-lower alkyl,
$R^2$ represents hydrogen, halogen, lower alkyl, phenyl, halo-lower alkyl or phenoxy,
l is 0 to 1,
m is an integer from 1 to 4,
n is an integer from 1 to 5, and
A-W-B represents a member selected from the group consisting of

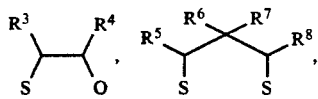

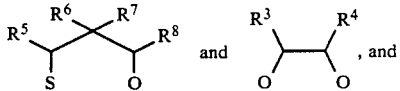

in which
$R^3$ and $R^4$ each represent hydrogen, hydroxy lower alkyl, lower alkoxy-lower alkyl, benzyloxy-lower alkyl, halo-lower alkyl or carboxy-lower alkyl, or
$R^3$ and $R^4$ form a hydrocarbon ring having 3 to 12 carbon atoms in total together with the carbon atoms to which then are bonded, and
$R^5$, $R^6$, $R^7$ and $R^8$ each represent hydrogen, lower alkyl or hydroxy-lower alkyl.

2. A 3-substituted pyridine according to claim 1, wherein
$R^1$ represents hydrogen or chlorine,
$R^2$ represents hydrogen, chlorine, bromine, fluorine, alkyl having 1 to 4 carbon atoms, or phenyl,
m and n are each 1 to 2,
$R^3$ and $R^4$ each represent hydrogen, alkyl having 1 to 6 carbon atoms, hydroxyalkyl having 1 to 3 carbon atoms, alkoxyalkyl having 2 to 4 carbon atoms in total or haloalkyl having 1 to 4 carbon atoms, or
$R^3$ and $R^4$ form a hydrocarbon ring having 6 to 12 carbon atoms in total together with the carbon atoms to which they are bonded, and
$R^5$, $R^6$, $R^7$ and $R^8$ each represent hydrogen, alkyl having one to four carbon atoms or hydroxyalkyl having 1 to 4 carbon atoms.

3. A 3-substituted pyridine according to claim 1, wherein
$R^1$ represents hydrogen or chlorine,
$R^2$ represents hydrogen, chlorine, bromine, fluorine, methyl or phenyl,
n and m are each 1 to 2,
$R^3$ and $R^4$ represent hydrogen, alkyl having 1 to 4 carbon atoms, methoxymethyl or chloromethyl, or
$R^3$ and $R^4$ form a cyclohexane ring together with the carbon atoms to which they are bonded, and
$R^5$, $R^6$, $R^7$ and $R^8$ each represent hydrogen or alkyl having 1 to 3 carbon atoms.

4. A fungicidal or herbicidal composition comprising a fungicidally or herbicidally effective amount of a compound according to claim 1 and a diluent.

5. A method of combating fungi which comprises applying to such fungi or to a fungus habitat a fungicidally effective amount of a compound according to claim 1.

6. A method of combating unwanted vegetation which comprises applying to such vegetation or to a locus from which is desired to exclude such vegetation a herbicidally effective amount of a compound according to claim 1.